United States Patent
Jamous et al.

(10) Patent No.: US 11,871,958 B2
(45) Date of Patent: *Jan. 16, 2024

(54) TISSUE-REMOVING CATHETER WITH GUIDEWIRE ISOLATION LINER

(71) Applicant: Medtronic Vascular, Inc., Santa Rosa, CA (US)

(72) Inventors: Aram Jamous, Athenry (IE); John Kelly, Galway (IE); Conor McMullen, Galway (IE); Matthew Fleming, Roscommon (IE); Colin William Meade, Westmeath (IE); Grainne Teresa Carroll, Galway (IE); Paul Morton, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 17/241,007

(22) Filed: Apr. 26, 2021

(65) Prior Publication Data
US 2021/0275209 A1    Sep. 9, 2021

Related U.S. Application Data

(63) Continuation of application No. 15/970,736, filed on May 3, 2018, now Pat. No. 10,987,126.
(Continued)

(51) Int. Cl.
  *A61B 17/3207*    (2006.01)
  *A61B 17/3205*    (2006.01)
  (Continued)

(52) U.S. Cl.
  CPC ............... *A61B 17/320758* (2013.01); *A61B 17/00234* (2013.01); *A61B 17/32002* (2013.01);
  (Continued)

(58) Field of Classification Search
  CPC ...... A61B 17/320758; A61B 17/32002; A61B 17/00234; A61B 2017/320004;
  (Continued)

(56) References Cited

U.S. PATENT DOCUMENTS

| 182,499 A | 9/1876 | Waterman |
| 639,898 A | 12/1899 | Huenefeld |

(Continued)

FOREIGN PATENT DOCUMENTS

| AU | 2007271820 A1 | 2/2009 |
| AU | 2009255433 A1 | 11/2010 |

(Continued)

OTHER PUBLICATIONS

US 7,316,661 B2, 01/2008, Zadno Azizi (withdrawn)
(Continued)

*Primary Examiner* — Tuan V Nguyen
(74) *Attorney, Agent, or Firm* — Stinson LLP

(57) ABSTRACT

A tissue-removing catheter for removing tissue in a body lumen includes an elongate body having an axis, and proximal and distal end portions spaced apart from one another along the axis. The elongate body is sized and shaped to be received in the body lumen. A tissue-removing element is mounted on the distal end portion of the elongate body. The tissue-removing element is configured to remove the tissue as the tissue-removing element is rotated by the elongate body within the body lumen. An inner liner is received within the elongate body and defines a guidewire lumen. The inner liner is coupled to the tissue-removing element at a distal end portion of the inner liner. A coupling assembly is disposed in the tissue-removing element for coupling the inner liner to the tissue-removing element. The coupling assembly includes a bushing attached directly to the distal end portion of the inner liner.

22 Claims, 9 Drawing Sheets

Related U.S. Application Data

(60) Provisional application No. 62/500,867, filed on May 3, 2017, provisional application No. 62/500,879, filed on May 3, 2017.

(51) Int. Cl.
*A61M 25/00* (2006.01)
*A61B 17/00* (2006.01)
*A61B 17/32* (2006.01)
*A61B 17/22* (2006.01)
*A61B 90/00* (2016.01)
*A61M 25/01* (2006.01)

(52) U.S. Cl.
CPC .................. *A61B 17/32053* (2013.01); *A61B 17/320783* (2013.01); *A61M 25/0082* (2013.01); *A61B 2017/0088* (2013.01); *A61B 2017/00292* (2013.01); *A61B 2017/00398* (2013.01); *A61B 2017/00477* (2013.01); *A61B 2017/00738* (2013.01); *A61B 2017/00845* (2013.01); *A61B 2017/22001* (2013.01); *A61B 2017/22038* (2013.01); *A61B 2017/320004* (2013.01); *A61B 2017/320024* (2013.01); *A61B 2017/320052* (2013.01); *A61B 2017/320064* (2013.01); *A61B 2017/320741* (2013.01); *A61B 2017/320775* (2013.01); *A61B 2090/0801* (2016.02); *A61M 25/0108* (2013.01); *A61M 2025/0096* (2013.01)

(58) Field of Classification Search
CPC ....... A61B 2017/320775; A61B 2017/320064; A61B 2017/320024; A61B 2017/320741; A61B 2017/00292

See application file for complete search history.

(56) References Cited

U.S. PATENT DOCUMENTS

| | | |
|---|---|---|
| 766,433 A | 8/1904 | Von |
| 970,748 A | 9/1910 | Post |
| 1,045,879 A | 12/1912 | Peterson |
| 2,099,368 A | 11/1937 | Lucien |
| 2,203,121 A | 6/1940 | Philipp |
| 2,280,657 A | 4/1942 | Mccandliss |
| 2,282,688 A | 5/1942 | Zuck |
| 2,303,149 A | 11/1942 | Verhagen |
| 2,303,151 A | 11/1942 | Watkins et al. |
| 2,398,405 A | 4/1946 | Brooks |
| 2,429,356 A | 10/1947 | Carter |
| 2,579,791 A | 12/1951 | Carter |
| 2,742,881 A | 4/1956 | Rideout et al. |
| 3,141,201 A | 7/1964 | Hermann et al. |
| 3,166,512 A | 1/1965 | Mizuno |
| 4,445,509 A | 5/1984 | Auth |
| 4,631,052 A | 12/1986 | Kensey et al. |
| 4,650,466 A | 3/1987 | Luther |
| 4,679,557 A | 7/1987 | Opie et al. |
| 4,729,763 A | 3/1988 | Henrie |
| 4,784,636 A | 11/1988 | Rydell |
| 4,795,438 A | 1/1989 | Kensey et al. |
| 4,829,999 A | 5/1989 | Auth |
| 4,850,957 A | 7/1989 | Summers |
| 4,857,046 A | 8/1989 | Stevens et al. |
| 4,883,460 A | 11/1989 | Zanetti |
| 4,886,061 A | 12/1989 | Fischell et al. |
| 4,890,611 A | 1/1990 | Monfort et al. |
| 4,895,560 A | 1/1990 | Papantonakos |
| 4,917,085 A | 4/1990 | Smith |
| 4,950,238 A | 8/1990 | Sullivan |
| 4,990,134 A | 2/1991 | Auth |
| 5,030,201 A | 7/1991 | Palestrant |
| 5,041,082 A | 8/1991 | Shiber |
| 5,049,124 A | 9/1991 | Bales, Jr. |
| 5,059,203 A | 10/1991 | Husted |
| 5,100,425 A | 3/1992 | Fischell et al. |
| 5,113,613 A | 5/1992 | Ackeret |
| 5,116,350 A | 5/1992 | Stevens |
| 5,116,352 A | 5/1992 | Schnepp et al. |
| 5,120,516 A | 6/1992 | Ham et al. |
| 5,126,667 A | 6/1992 | Kataoka et al. |
| 5,129,698 A | 7/1992 | Cohrs et al. |
| 5,129,734 A | 7/1992 | Van Erden |
| 5,158,564 A | 10/1992 | Schnepp et al. |
| 5,160,342 A | 11/1992 | Reger et al. |
| 5,165,187 A | 11/1992 | Shahidi Hamedani et al. |
| 5,170,805 A | 12/1992 | Kensey et al. |
| 5,176,693 A | 1/1993 | Pannek, Jr. |
| 5,178,625 A | 1/1993 | Groshong |
| 5,193,735 A | 3/1993 | Knight |
| 5,195,954 A | 3/1993 | Schnepp et al. |
| 5,221,087 A | 6/1993 | Fenton et al. |
| 5,242,460 A | 9/1993 | Klein et al. |
| 5,242,461 A | 9/1993 | Kortenbach et al. |
| 5,250,060 A | 10/1993 | Carbo |
| 5,267,955 A | 12/1993 | Hanson |
| 5,287,858 A | 2/1994 | Hammerslag et al. |
| 5,295,958 A | 3/1994 | Shturman |
| 5,308,354 A | 5/1994 | Zacca et al. |
| 5,312,427 A | 5/1994 | Zacca et al. |
| 5,314,407 A | 5/1994 | Auth et al. |
| 5,314,438 A | 5/1994 | Shturman |
| 5,318,576 A | 6/1994 | Plassche, Jr. et al. |
| 5,344,395 A | 9/1994 | Whalen et al. |
| 5,356,481 A | 10/1994 | Yoshimura et al. |
| 5,360,432 A | 11/1994 | Shturman |
| 5,366,463 A | 11/1994 | Ryan |
| 5,366,464 A | 11/1994 | Belknap |
| 5,376,077 A | 12/1994 | Gomringer |
| 5,376,100 A | 12/1994 | Lefebvre |
| 5,417,703 A | 5/1995 | Brown et al. |
| 5,490,859 A | 2/1996 | Mische et al. |
| 5,501,694 A | 3/1996 | Ressemann et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,540,707 A | 7/1996 | Ressemann et al. |
| 5,554,163 A | 9/1996 | Shturman |
| 5,569,275 A | 10/1996 | Kotula et al. |
| 5,569,276 A | 10/1996 | Jang et al. |
| 5,571,136 A | 11/1996 | Weaver |
| 5,584,843 A | 12/1996 | Wulfman et al. |
| 5,626,562 A | 5/1997 | Castro |
| 5,628,761 A | 5/1997 | Rizik |
| 5,632,755 A | 5/1997 | Nordgren |
| 5,634,897 A | 6/1997 | Dance et al. |
| 5,667,490 A | 9/1997 | Keith et al. |
| 5,681,336 A | 10/1997 | Clement et al. |
| 5,685,718 A | 11/1997 | Mcclintic |
| 5,701,119 A | 12/1997 | Jurras, III |
| 5,723,390 A | 3/1998 | Kijima et al. |
| 5,728,063 A | 3/1998 | Preissman et al. |
| 5,728,123 A | 3/1998 | Lemelson et al. |
| 5,728,129 A | 3/1998 | Summers |
| 5,766,190 A | 6/1998 | Wulfman |
| 5,766,192 A | 6/1998 | Zacca |
| 5,779,721 A | 7/1998 | Nash |
| 5,792,157 A | 8/1998 | Mische et al. |
| 5,800,083 A | 9/1998 | Gaarder et al. |
| 5,836,868 A | 11/1998 | Ressemann et al. |
| 5,836,957 A | 11/1998 | Schulz et al. |
| 5,843,103 A | 12/1998 | Wulfman |
| 5,843,150 A | 12/1998 | Dreessen et al. |
| 5,855,601 A | 1/1999 | Bessler et al. |
| 5,868,767 A | 2/1999 | Farley et al. |
| 5,895,397 A | 4/1999 | Jang et al. |
| 5,895,399 A | 4/1999 | Barbut et al. |
| 5,895,400 A | 4/1999 | Abela |
| 5,895,402 A | 4/1999 | Hundertmark et al. |
| 5,897,566 A | 4/1999 | Shturman et al. |
| 5,897,567 A | 4/1999 | Ressemann et al. |

(56) References Cited

U.S. PATENT DOCUMENTS

| | | |
|---|---|---|
| 5,904,698 A | 5/1999 | Thomas et al. |
| 5,916,227 A | 6/1999 | Keith et al. |
| 5,916,234 A | 6/1999 | Lam |
| 5,919,200 A | 7/1999 | Stambaugh et al. |
| 5,925,055 A | 7/1999 | Adrian et al. |
| 5,938,670 A | 8/1999 | Keith et al. |
| 5,954,747 A | 9/1999 | Lee |
| 5,961,534 A | 10/1999 | Banik et al. |
| 5,976,165 A | 11/1999 | Ball et al. |
| 5,989,208 A | 11/1999 | Nita |
| 5,997,557 A | 12/1999 | Barbut et al. |
| 6,010,449 A | 1/2000 | Selmon et al. |
| 6,010,622 A | 1/2000 | Chinn et al. |
| 6,015,420 A | 1/2000 | Wulfman et al. |
| 6,027,450 A | 2/2000 | Brown et al. |
| 6,039,747 A | 3/2000 | Shturman et al. |
| 6,059,812 A | 5/2000 | Clerc et al. |
| 6,077,282 A | 6/2000 | Shturman et al. |
| 6,080,171 A | 6/2000 | Keith et al. |
| RE36,764 E | 7/2000 | Zacca et al. |
| 6,083,228 A | 7/2000 | Michelson |
| 6,090,135 A | 7/2000 | Plaia et al. |
| 6,093,157 A | 7/2000 | Chandrasekaran |
| 6,096,054 A | 8/2000 | Wyzgala et al. |
| 6,099,534 A | 8/2000 | Bates et al. |
| 6,113,579 A | 9/2000 | Eidenschink et al. |
| 6,113,613 A | 9/2000 | Spaulding |
| 6,113,614 A | 9/2000 | Mears |
| 6,113,615 A | 9/2000 | Wulfman |
| 6,120,516 A | 9/2000 | Selmon et al. |
| 6,120,517 A | 9/2000 | Daum et al. |
| 6,126,667 A | 10/2000 | Barry et al. |
| 6,129,698 A | 10/2000 | Beck |
| 6,129,734 A | 10/2000 | Shturman et al. |
| 6,132,444 A | 10/2000 | Shturman |
| 6,146,395 A | 11/2000 | Kanz |
| 6,156,046 A | 12/2000 | Passafaro et al. |
| 6,165,187 A | 12/2000 | Reger |
| 6,165,209 A | 12/2000 | Patterson et al. |
| 6,183,487 B1 | 2/2001 | Lawrence |
| 6,193,735 B1 | 2/2001 | Stevens |
| 6,217,595 B1 | 4/2001 | Shturman et al. |
| 6,221,015 B1 | 4/2001 | Yock |
| 6,221,087 B1 | 4/2001 | Anderson et al. |
| 6,235,042 B1 | 5/2001 | Katzman |
| 6,245,007 B1 | 6/2001 | Bedingham |
| 6,251,121 B1 | 6/2001 | Saadat |
| 6,258,052 B1 | 7/2001 | Milo |
| 6,266,550 B1 | 7/2001 | Selmon et al. |
| 6,270,509 B1 | 8/2001 | Lawrence |
| 6,295,712 B1 | 10/2001 | Shturman et al. |
| 6,299,623 B1 | 10/2001 | Wulfman |
| 6,300,434 B1 | 10/2001 | Schwager et al. |
| 6,306,151 B1 | 10/2001 | Lary |
| 6,312,444 B1 | 11/2001 | Barbut |
| 6,319,242 B1 | 11/2001 | Patterson et al. |
| 6,328,750 B1 | 12/2001 | Berry |
| 6,343,605 B1 | 2/2002 | Lafontaine |
| 6,375,609 B1 | 4/2002 | Hastings et al. |
| 6,391,832 B2 | 5/2002 | Lyons et al. |
| 6,398,798 B2 | 6/2002 | Selmon et al. |
| 6,400,980 B1 | 6/2002 | Lemelson |
| 6,416,523 B1 | 7/2002 | Lafontaine |
| 6,416,526 B1 | 7/2002 | Wyzgala et al. |
| 6,425,904 B1 | 7/2002 | Lemelson |
| 6,428,552 B1 | 8/2002 | Sparks et al. |
| 6,434,507 B1 | 8/2002 | Clayton et al. |
| 6,436,111 B1 | 8/2002 | Kadavy et al. |
| 6,440,503 B1 | 8/2002 | Merdan et al. |
| 6,443,967 B1 | 9/2002 | Kadavy et al. |
| 6,443,979 B1 | 9/2002 | Stalker et al. |
| 6,451,037 B1 | 9/2002 | Chandraskaran et al. |
| 6,461,383 B1 | 10/2002 | Gesswein et al. |
| 6,468,227 B2 | 10/2002 | Zimmon |
| 6,475,225 B1 | 11/2002 | Wulfman et al. |
| 6,478,807 B1 | 11/2002 | Foreman et al. |
| 6,482,209 B1 | 11/2002 | Engh et al. |
| 6,482,215 B1 | 11/2002 | Shiber |
| 6,482,216 B1 | 11/2002 | Hiblar et al. |
| 6,488,654 B2 | 12/2002 | Gonzalez et al. |
| 6,491,660 B2 | 12/2002 | Guo et al. |
| 6,494,890 B1 | 12/2002 | Shturman |
| 6,497,711 B1 | 12/2002 | Plaia et al. |
| 6,500,186 B2 | 12/2002 | Lafontaine et al. |
| 6,503,227 B1 | 1/2003 | Guo et al. |
| 6,503,261 B1 | 1/2003 | Bruneau et al. |
| 6,517,544 B1 | 2/2003 | Michelson |
| 6,537,202 B1 | 3/2003 | Frantzen |
| 6,537,279 B1 | 3/2003 | Michelson |
| 6,540,719 B2 | 4/2003 | Bigus et al. |
| 6,554,846 B2 | 4/2003 | Hamilton et al. |
| 6,562,049 B1 | 5/2003 | Norlander et al. |
| 6,569,177 B1 | 5/2003 | Dillard et al. |
| 6,572,630 B1 | 6/2003 | McGuckin, Jr. et al. |
| 6,579,298 B1 | 6/2003 | Bruneau et al. |
| 6,579,299 B2 | 6/2003 | McGuckin, Jr. et al. |
| 6,589,251 B2 | 7/2003 | Yee |
| 6,596,005 B1 | 7/2003 | Kanz |
| 6,602,265 B2 | 8/2003 | Dubrul et al. |
| 6,613,066 B1 | 9/2003 | Fukaya et al. |
| 6,613,075 B1 | 9/2003 | Healy |
| 6,616,676 B2 | 9/2003 | Bashiri |
| 6,620,179 B2 | 9/2003 | Book et al. |
| 6,626,861 B1 | 9/2003 | Hart et al. |
| 6,626,923 B1 | 9/2003 | Wyzgala |
| 6,632,230 B2 | 10/2003 | Barry |
| 6,638,228 B1 | 10/2003 | Chandrasekaran et al. |
| 6,638,288 B1 | 10/2003 | Shturman et al. |
| 6,652,548 B2 | 11/2003 | Evans et al. |
| 6,669,710 B2 | 12/2003 | Moutafis et al. |
| 6,682,543 B2 | 1/2004 | Barbut et al. |
| 6,685,718 B1 | 2/2004 | Wyzgala et al. |
| 6,702,834 B1 | 3/2004 | Boylan |
| 6,719,775 B2 | 4/2004 | Slaker et al. |
| 6,719,781 B1 | 4/2004 | Kim |
| 6,723,390 B2 | 4/2004 | Merdan et al. |
| 6,761,733 B2 | 7/2004 | Chobotov et al. |
| 6,764,498 B2 | 7/2004 | Mische |
| 6,786,876 B2 | 9/2004 | Cox |
| 6,790,215 B2 | 9/2004 | Findlay |
| 6,792,979 B2 | 9/2004 | Konya et al. |
| 6,800,083 B2 | 10/2004 | Hiblar et al. |
| 6,800,085 B2 | 10/2004 | Selmon et al. |
| 6,800,086 B2 | 10/2004 | Strong |
| 6,808,531 B2 | 10/2004 | Lafontaine et al. |
| 6,827,734 B2 | 12/2004 | Fariabi |
| 6,837,890 B1 | 1/2005 | Chludzinski et al. |
| 6,852,097 B1 | 2/2005 | Fulton |
| 6,852,118 B2 | 2/2005 | Shturman et al. |
| 6,872,204 B2 | 3/2005 | Houser et al. |
| 6,884,235 B2 | 4/2005 | McGuckin, Jr. et al. |
| 6,899,712 B2 | 5/2005 | Moutafis et al. |
| 6,911,026 B1 | 6/2005 | Hall et al. |
| 6,939,352 B2 | 9/2005 | Buzzard et al. |
| 6,951,554 B2 | 10/2005 | Johansen et al. |
| 6,951,570 B2 | 10/2005 | Linder et al. |
| 6,953,468 B2 | 10/2005 | Jones et al. |
| 6,986,778 B2 | 1/2006 | Zadno et al. |
| 7,004,173 B2 | 2/2006 | Sparks et al. |
| 7,027,460 B2 | 4/2006 | Iyer et al. |
| 7,063,714 B2 | 6/2006 | Dorros et al. |
| 7,141,045 B2 | 11/2006 | Johansson et al. |
| 7,169,118 B2 | 1/2007 | Reynolds et al. |
| 7,172,571 B2 | 2/2007 | Moskowitz et al. |
| 7,179,269 B2 | 2/2007 | Welch et al. |
| 7,189,240 B1 | 3/2007 | Dekel |
| 7,211,041 B2 | 5/2007 | Mueller |
| 7,217,255 B2 | 5/2007 | Boyle et al. |
| 7,247,269 B2 | 7/2007 | Keidar |
| 7,252,674 B2 | 8/2007 | Wyzgala et al. |
| 7,311,719 B2 | 12/2007 | Bonutti |
| 7,344,546 B2 | 3/2008 | Wulfman et al. |
| 7,381,216 B2 | 6/2008 | Buzzard et al. |
| 7,384,407 B2 | 6/2008 | Rodriguez et al. |

(56) References Cited

U.S. PATENT DOCUMENTS

| | | |
|---|---|---|
| 7,485,127 B2 | 2/2009 | Nistal |
| 7,494,485 B2 | 2/2009 | Beck et al. |
| 7,507,245 B2 | 3/2009 | Shturman et al. |
| 7,513,886 B2 | 4/2009 | Konstantino |
| 7,517,352 B2 | 4/2009 | Evans et al. |
| 7,534,249 B2 | 5/2009 | Nash et al. |
| 7,537,588 B2 | 5/2009 | Palasis et al. |
| 7,582,112 B2 | 9/2009 | Scheuemann et al. |
| 7,585,300 B2 | 9/2009 | Cha |
| 7,591,996 B2 | 9/2009 | Hwang et al. |
| 7,594,900 B1 | 9/2009 | Nash et al. |
| 7,618,434 B2 | 11/2009 | Santra et al. |
| D607,102 S | 12/2009 | Robinson |
| 7,632,301 B2 | 12/2009 | Alt |
| 7,645,290 B2 | 1/2010 | Lucas |
| D610,258 S | 2/2010 | Robinson |
| 7,670,327 B2 | 3/2010 | Kucharczyk et al. |
| 7,674,272 B2 | 3/2010 | Torrance et al. |
| 7,686,824 B2 | 3/2010 | Konstantino et al. |
| 7,687,144 B2 | 3/2010 | Clark et al. |
| 7,691,121 B2 | 4/2010 | Rosenbluth et al. |
| 7,697,996 B2 | 4/2010 | Manning et al. |
| 7,699,865 B2 | 4/2010 | Johnson et al. |
| 7,715,896 B2 | 5/2010 | Ramzipoor et al. |
| 7,731,731 B2 | 6/2010 | Abela |
| 7,734,332 B2 | 6/2010 | Sher |
| 7,744,587 B2 | 6/2010 | Murphy |
| 7,749,266 B2 | 7/2010 | Forster et al. |
| 7,758,604 B2 | 7/2010 | Wu et al. |
| 7,789,860 B2 | 9/2010 | Brady et al. |
| 7,819,863 B2 | 10/2010 | Eggers et al. |
| 7,832,406 B2 | 11/2010 | Ellis et al. |
| 7,833,240 B2 | 11/2010 | Okushi et al. |
| 7,854,755 B2 | 12/2010 | Lafontaine et al. |
| 7,887,557 B2 | 2/2011 | Kelley et al. |
| 7,909,873 B2 | 3/2011 | Tan-Malecki et al. |
| 7,922,650 B2 | 4/2011 | McWeeney et al. |
| 7,938,851 B2 | 5/2011 | Olson et al. |
| 7,951,161 B2 | 5/2011 | Bonnette et al. |
| 7,963,915 B2 | 6/2011 | Bleich |
| 7,967,790 B2 | 6/2011 | Whiting et al. |
| 7,967,834 B2 | 6/2011 | Tal et al. |
| 7,976,460 B2 | 7/2011 | Richardson |
| 7,985,200 B2 | 7/2011 | Lary et al. |
| 7,993,384 B2 | 8/2011 | Wu et al. |
| 7,997,226 B2 | 8/2011 | Diaz et al. |
| 8,002,725 B2 | 8/2011 | Hogendijk |
| 8,011,316 B2 | 9/2011 | Diaz et al. |
| 8,012,153 B2 | 9/2011 | Woloszko et al. |
| 8,021,379 B2 | 9/2011 | Thompson et al. |
| 8,043,287 B2 | 10/2011 | Conquergood et al. |
| 8,043,362 B2 | 10/2011 | Gong et al. |
| 8,052,637 B2 | 11/2011 | Von Oepen et al. |
| 8,052,716 B2 | 11/2011 | Gilson et al. |
| 8,062,298 B2 | 11/2011 | Schmitz et al. |
| 8,067,055 B2 | 11/2011 | Savage et al. |
| 8,080,026 B2 | 12/2011 | Konstantino et al. |
| 8,083,713 B2 | 12/2011 | Smith et al. |
| 8,105,351 B2 | 1/2012 | Lehman et al. |
| 8,109,954 B2 | 2/2012 | Shturman |
| 8,109,955 B2 | 2/2012 | Shturman |
| 8,123,750 B2 | 2/2012 | Norton et al. |
| 8,123,776 B2 | 2/2012 | Gilson et al. |
| 8,134,041 B2 | 3/2012 | Etchells |
| 8,137,369 B2 | 3/2012 | Shturman |
| 8,142,457 B2 | 3/2012 | Lafontaine |
| 8,147,507 B2 | 4/2012 | Shtruman |
| 8,157,825 B2 | 4/2012 | Shtruman |
| 8,158,670 B2 | 4/2012 | Kunz et al. |
| 8,162,964 B2 | 4/2012 | Piippo et al. |
| 8,175,677 B2 | 5/2012 | Sayler et al. |
| 8,177,801 B2 | 5/2012 | Kallock et al. |
| 8,182,499 B2 | 5/2012 | Abraham et al. |
| 8,192,402 B2 | 6/2012 | Anderson et al. |
| 8,192,451 B2 | 6/2012 | Cambronne et al. |
| 8,208,990 B2 | 6/2012 | Maschke |
| 8,221,348 B2 | 7/2012 | Hackett et al. |
| 8,241,335 B2 | 8/2012 | Truckai et al. |
| 8,308,711 B2 | 11/2012 | Lee et al. |
| 8,308,790 B2 | 11/2012 | Arbefeuille et al. |
| 8,317,786 B2 | 11/2012 | Dahla et al. |
| 8,323,249 B2 | 12/2012 | Wulfman et al. |
| 8,323,261 B2 | 12/2012 | Kugler et al. |
| 8,323,279 B2 | 12/2012 | Dahla et al. |
| 8,337,518 B2 | 12/2012 | Nance et al. |
| 8,348,965 B2 | 1/2013 | Prudnikov et al. |
| 8,348,987 B2 | 1/2013 | Eaton |
| 8,353,923 B2 | 1/2013 | Shturman |
| 8,353,944 B2 | 1/2013 | Weber et al. |
| 8,377,037 B2 | 2/2013 | Sachdeva et al. |
| 8,382,423 B1 | 2/2013 | Frodis et al. |
| 8,382,739 B2 | 2/2013 | Walak |
| 8,388,582 B2 | 3/2013 | Eubanks et al. |
| 8,388,636 B2 | 3/2013 | Shturman |
| 8,388,637 B2 | 3/2013 | Shturman |
| 8,398,663 B2 | 3/2013 | Paul et al. |
| 8,435,228 B2 | 5/2013 | Wulfman et al. |
| 8,439,937 B2 | 5/2013 | Montague et al. |
| 8,449,566 B2 | 5/2013 | Finitsis |
| 8,454,638 B2 | 6/2013 | Shturman |
| 8,465,510 B2 | 6/2013 | Shturman |
| 8,475,478 B2 | 7/2013 | Robinson |
| 8,475,487 B2 | 7/2013 | Bonnette et al. |
| 8,480,628 B2 | 7/2013 | Hawkins et al. |
| 8,496,678 B2 | 7/2013 | Shturman |
| 8,500,764 B2 | 8/2013 | Shturman |
| 8,500,765 B2 | 8/2013 | Shturman |
| 8,524,132 B2 | 9/2013 | Von Oepen et al. |
| 8,529,614 B2 | 9/2013 | Berez et al. |
| 8,530,783 B2 | 9/2013 | Ow et al. |
| 8,532,746 B2 | 9/2013 | Gelbart et al. |
| 8,551,128 B2 | 10/2013 | Hanson et al. |
| 8,551,130 B2 | 10/2013 | Schoenle et al. |
| 8,562,607 B2 | 10/2013 | Truckai et al. |
| 8,568,432 B2 | 10/2013 | Straub |
| 8,579,926 B2 | 11/2013 | Pinto et al. |
| 8,597,239 B2 | 12/2013 | Gerrans et al. |
| 8,597,313 B2 | 12/2013 | Thatcher et al. |
| 8,603,038 B2 | 12/2013 | Nelson |
| 8,612,022 B1 | 12/2013 | Morero et al. |
| 8,613,721 B2 | 12/2013 | Wulfman |
| 8,617,144 B2 | 12/2013 | Ravikumar |
| 8,628,550 B2 | 1/2014 | Narveson |
| 8,628,551 B2 | 1/2014 | Hanson et al. |
| 8,632,556 B2 | 1/2014 | Jacobs et al. |
| 8,632,557 B2 | 1/2014 | Thatcher et al. |
| 8,657,821 B2 | 2/2014 | Palermo |
| 8,663,195 B2 | 3/2014 | Shturman |
| 8,663,228 B2 | 3/2014 | Schmitz et al. |
| 8,663,260 B2 | 3/2014 | Shturman |
| 8,663,261 B2 | 3/2014 | Shturman |
| 8,679,141 B2 | 3/2014 | Goodin et al. |
| 8,684,952 B2 | 4/2014 | Weitzner et al. |
| 8,696,645 B2 | 4/2014 | Tal et al. |
| 8,702,652 B2 | 4/2014 | Fiorella et al. |
| 8,702,735 B2 | 4/2014 | Rivers |
| 8,709,087 B2 | 4/2014 | Cragg |
| 8,715,227 B2 | 5/2014 | Kontos |
| 8,715,240 B2 | 5/2014 | Cunningham |
| 8,728,106 B2 | 5/2014 | Weber et al. |
| 8,758,325 B2 | 6/2014 | Webster et al. |
| 8,758,377 B2 | 6/2014 | Rivers et al. |
| 8,771,302 B2 | 7/2014 | Woolfson et al. |
| 8,779,328 B2 | 7/2014 | Anukhin et al. |
| 8,790,299 B2 | 7/2014 | Gunday et al. |
| 8,792,962 B2 | 7/2014 | Esguerra et al. |
| 8,795,241 B2 | 8/2014 | O'Connell et al. |
| 8,795,303 B2 | 8/2014 | McBroom et al. |
| 8,795,304 B2 | 8/2014 | Piippovendsen |
| 8,814,892 B2 | 8/2014 | Galdonik et al. |
| 8,827,951 B2 | 9/2014 | Besser et al. |
| 8,840,566 B2 | 9/2014 | Seibel et al. |
| 8,864,762 B2 | 10/2014 | Gunday et al. |
| 8,882,697 B2 | 11/2014 | Celermajer |

(56) References Cited

U.S. PATENT DOCUMENTS

| | | |
|---|---|---|
| 8,882,790 B2 | 11/2014 | Kassab et al. |
| 8,888,787 B2 | 11/2014 | Wynberg |
| 8,920,402 B2 | 12/2014 | Nash et al. |
| 8,926,560 B2 | 1/2015 | Dinh et al. |
| 8,932,694 B2 | 1/2015 | Rolfes et al. |
| 8,936,589 B2 | 1/2015 | Shturman |
| 8,945,089 B2 | 2/2015 | Johnson et al. |
| 8,951,224 B2 | 2/2015 | Wulfman et al. |
| 8,961,533 B2 | 2/2015 | Stahler et al. |
| 8,968,346 B2 | 3/2015 | Lockard et al. |
| 8,974,519 B2 | 3/2015 | Gennrich et al. |
| 8,986,331 B2 | 3/2015 | Chekan et al. |
| 8,992,553 B2 | 3/2015 | Diamant et al. |
| 8,992,557 B2 | 3/2015 | Whayne et al. |
| 8,992,717 B2 | 3/2015 | Zeroni et al. |
| 8,998,843 B2 | 4/2015 | Bonnette et al. |
| 9,017,294 B2 | 4/2015 | McGuckin, Jr. et al. |
| 9,050,127 B2 | 6/2015 | Bonnette et al. |
| 9,050,414 B2 | 6/2015 | Schoenle et al. |
| 9,055,951 B2 | 6/2015 | Deshpande |
| 9,055,966 B2 | 6/2015 | Cambronne et al. |
| 9,072,873 B2 | 7/2015 | Lippert et al. |
| 9,078,692 B2 | 7/2015 | Shturman et al. |
| 9,078,779 B2 | 7/2015 | Dorn et al. |
| 9,084,620 B2 | 7/2015 | Ludin et al. |
| 9,084,627 B2 | 7/2015 | Weber |
| 9,089,362 B2 | 7/2015 | Shturman |
| 9,101,382 B2 | 8/2015 | Krolik et al. |
| 9,101,387 B2 | 8/2015 | Plowe et al. |
| 9,101,430 B2 | 8/2015 | Müller |
| 9,108,027 B2 | 8/2015 | Eubanks et al. |
| 9,114,235 B2 | 8/2015 | Cambronne |
| 9,119,662 B2 | 9/2015 | Moberg |
| 9,119,944 B2 | 9/2015 | Chambers et al. |
| 9,138,210 B2 | 9/2015 | Schulte et al. |
| 9,162,040 B2 | 10/2015 | Vo et al. |
| 9,162,046 B2 | 10/2015 | Hill et al. |
| 9,174,019 B2 | 11/2015 | Gregersen |
| 9,180,274 B2 | 11/2015 | Cully et al. |
| 9,186,129 B2 | 11/2015 | Blitzer et al. |
| 9,186,170 B2 | 11/2015 | Welty et al. |
| 9,186,210 B2 | 11/2015 | Jenson |
| 9,192,405 B2 | 11/2015 | Shturman |
| 9,199,058 B2 | 12/2015 | Lentz |
| 9,205,234 B2 | 12/2015 | Hardin |
| 9,211,138 B2 | 12/2015 | Shturman |
| 9,211,386 B2 | 12/2015 | Aboytes |
| 9,216,033 B2 | 12/2015 | Feld et al. |
| 9,216,034 B2 | 12/2015 | Avneri |
| 9,217,442 B2 | 12/2015 | Wiessler et al. |
| 9,220,529 B2 | 12/2015 | Rivers et al. |
| 9,220,530 B2 | 12/2015 | Moberg |
| 9,226,763 B2 | 1/2016 | To et al. |
| 9,237,903 B2 | 1/2016 | Shturman |
| 9,238,126 B2 | 1/2016 | Gerrans et al. |
| 9,254,143 B2 | 2/2016 | Huynh et al. |
| 9,259,215 B2 | 2/2016 | Chou et al. |
| 9,265,563 B2 | 2/2016 | Racz et al. |
| 9,289,230 B2 | 3/2016 | Cambronne |
| 9,295,373 B2 | 3/2016 | Torrance et al. |
| 9,301,769 B2 | 4/2016 | Brady et al. |
| 9,301,774 B2 | 4/2016 | O'Day |
| 9,308,007 B2 | 4/2016 | Cully et al. |
| 9,308,019 B2 | 4/2016 | Kugler et al. |
| 9,314,324 B2 | 4/2016 | Janardhan et al. |
| 9,320,530 B2 | 4/2016 | Grace |
| 9,320,535 B2 | 4/2016 | Zaretzka et al. |
| 9,320,540 B2 | 4/2016 | Badie |
| 9,326,789 B2 | 5/2016 | Fruland et al. |
| 9,333,006 B2 | 5/2016 | Shturman |
| 9,333,335 B2 | 5/2016 | Ollivier et al. |
| 9,345,508 B2 | 5/2016 | Hendrick |
| 9,345,511 B2 | 5/2016 | Smith et al. |
| 9,345,858 B2 | 5/2016 | Flaherty et al. |
| 9,351,741 B2 | 5/2016 | Schmitz et al. |
| 9,351,757 B2 | 5/2016 | Kusleika |
| 9,364,255 B2 | 6/2016 | Weber |
| 9,364,256 B2 | 6/2016 | Shturman |
| 9,370,649 B2 | 6/2016 | Chang et al. |
| 9,375,234 B2 | 6/2016 | Vrba |
| 9,375,328 B2 | 6/2016 | Farnan |
| 9,381,062 B2 | 7/2016 | Kapur et al. |
| 9,387,006 B2 | 7/2016 | Shtruman |
| 9,387,305 B2 | 7/2016 | Courtney et al. |
| 9,398,837 B2 | 7/2016 | Vazales et al. |
| 9,402,981 B2 | 8/2016 | Anderson |
| 9,413,896 B2 | 8/2016 | Bowe et al. |
| 9,414,852 B2 | 8/2016 | Gifford, III et al. |
| 9,427,553 B2 | 8/2016 | Nelson |
| D766,433 S | 9/2016 | Blackledge et al. |
| 9,433,437 B2 | 9/2016 | Kesten et al. |
| 9,439,674 B2 | 9/2016 | Rydberg et al. |
| 9,445,829 B2 | 9/2016 | Brady et al. |
| 9,452,241 B2 | 9/2016 | Gill et al. |
| 9,456,843 B2 | 10/2016 | Kessler et al. |
| 9,463,041 B2 | 10/2016 | Bleich et al. |
| 9,468,457 B2 | 10/2016 | Blackledge et al. |
| 9,474,536 B2 | 10/2016 | Carrison et al. |
| 9,474,543 B2 | 10/2016 | McGuckin, Jr. et al. |
| 9,486,611 B2 | 11/2016 | Petersen et al. |
| 9,498,183 B2 | 11/2016 | Brown et al. |
| 9,498,290 B2 | 11/2016 | Piferi et al. |
| 9,510,885 B2 | 12/2016 | Burger et al. |
| 9,526,519 B2 | 12/2016 | Kessler et al. |
| 9,526,674 B2 | 12/2016 | Heyns et al. |
| 9,532,797 B2 | 1/2017 | Vreeman |
| 9,532,799 B2 | 1/2017 | Simpson et al. |
| 9,539,019 B2 | 1/2017 | Sullivan et al. |
| 9,545,298 B2 | 1/2017 | Ginn et al. |
| 9,561,347 B2 | 2/2017 | Holm et al. |
| 9,572,492 B2 | 2/2017 | Simpson et al. |
| 9,597,109 B2 | 3/2017 | Shturman |
| 9,597,110 B2 | 3/2017 | Kessler et al. |
| 9,675,376 B2 | 6/2017 | To et al. |
| 9,687,266 B2 | 6/2017 | Moberg et al. |
| 9,693,796 B2 | 7/2017 | Rydberg |
| 9,700,346 B2 | 7/2017 | Levine et al. |
| 9,700,347 B2 | 7/2017 | Shiber |
| 9,717,520 B2 | 8/2017 | Zeroni et al. |
| 9,750,509 B2 | 9/2017 | Carrison |
| 9,855,072 B2 | 1/2018 | Moberg |
| 9,901,252 B2 | 2/2018 | Tran |
| 10,413,318 B2 | 9/2019 | Grothe et al. |
| 10,786,278 B2 | 9/2020 | Nishio et al. |
| 10,869,689 B2 | 12/2020 | Fleming et al. |
| 10,925,632 B2 | 2/2021 | Jamous et al. |
| 10,987,126 B2 | 4/2021 | Jamous et al. |
| 11,051,842 B2 | 7/2021 | Jamous et al. |
| 2001/0018591 A1 | 8/2001 | Brock et al. |
| 2001/0047165 A1 | 11/2001 | Makower et al. |
| 2002/0007190 A1 | 1/2002 | Wulfman et al. |
| 2002/0029057 A1 | 3/2002 | McGuckin, Jr. |
| 2002/0098278 A1 | 7/2002 | Bates et al. |
| 2002/0151917 A1 | 10/2002 | Barry |
| 2003/0069522 A1 | 4/2003 | Jacobsen et al. |
| 2003/0109837 A1 | 6/2003 | McBride |
| 2003/0139689 A1 | 7/2003 | Shturman et al. |
| 2003/0144656 A1 | 7/2003 | Ocel et al. |
| 2003/0187498 A1 | 10/2003 | Bishop |
| 2003/0191435 A1 | 10/2003 | Shkolnik |
| 2003/0199889 A1 | 10/2003 | Kanz et al. |
| 2003/0236533 A1 | 12/2003 | Wilson et al. |
| 2004/0097995 A1 | 5/2004 | Nash et al. |
| 2004/0147934 A1 | 7/2004 | Kiester |
| 2004/0215222 A1 | 10/2004 | Krivoruchko |
| 2004/0225355 A1 | 11/2004 | Stevens |
| 2004/0267191 A1 | 12/2004 | Gifford et al. |
| 2005/0031495 A1 | 2/2005 | Choi et al. |
| 2005/0096633 A1 | 5/2005 | Moskowitz |
| 2005/0149083 A1 | 7/2005 | Prudnikov et al. |
| 2005/0149084 A1 | 7/2005 | Kanz et al. |
| 2005/0187537 A1 | 8/2005 | Loeb et al. |
| 2005/0187556 A1 | 8/2005 | Stack et al. |
| 2005/0203553 A1 | 9/2005 | Maschke |

(56) References Cited

U.S. PATENT DOCUMENTS

| | | |
|---|---|---|
| 2005/0216044 A1 | 9/2005 | Hong |
| 2005/0228417 A1 | 10/2005 | Teitelbaum et al. |
| 2005/0251187 A1 | 11/2005 | Beane et al. |
| 2005/0272976 A1 | 12/2005 | Tanaka et al. |
| 2006/0030934 A1 | 2/2006 | Hogendijk et al. |
| 2006/0047291 A1 | 3/2006 | Barry |
| 2006/0095059 A1 | 5/2006 | Bleich et al. |
| 2006/0142630 A1 | 6/2006 | Meretei |
| 2006/0142632 A1 | 6/2006 | Meretei |
| 2006/0253145 A1 | 11/2006 | Lucas |
| 2006/0264988 A1 | 11/2006 | Boyle |
| 2006/0271155 A1 | 11/2006 | Herr |
| 2007/0088230 A1 | 4/2007 | Terashi et al. |
| 2007/0093779 A1 | 4/2007 | Kugler et al. |
| 2007/0093781 A1 | 4/2007 | Kugler et al. |
| 2007/0135830 A1 | 6/2007 | Schaeffer |
| 2007/0203516 A1 | 8/2007 | Nayak |
| 2007/0213753 A1 | 9/2007 | Waller |
| 2007/0282367 A1 | 12/2007 | Jeffrey et al. |
| 2007/0287933 A1 | 12/2007 | Phan et al. |
| 2008/0033423 A1 | 2/2008 | Peacock |
| 2008/0033467 A1 | 2/2008 | Miyamoto et al. |
| 2008/0161840 A1 | 7/2008 | Osiroff et al. |
| 2008/0208230 A1 | 8/2008 | Chin |
| 2008/0221566 A1 | 9/2008 | Krishnan |
| 2008/0228208 A1 | 9/2008 | Wulfman et al. |
| 2008/0228209 A1 | 9/2008 | DeMello et al. |
| 2008/0306498 A1 | 12/2008 | Thatcher et al. |
| 2008/0312671 A1 | 12/2008 | Riles et al. |
| 2009/0018564 A1 | 1/2009 | Shturman |
| 2009/0069829 A1 | 3/2009 | Shturman |
| 2009/0112239 A1 | 4/2009 | To |
| 2009/0149865 A1 | 6/2009 | Schmitz et al. |
| 2009/0163940 A1 | 6/2009 | Sliwa |
| 2009/0182359 A1 | 7/2009 | Shturman |
| 2009/0182362 A1 | 7/2009 | Thompson et al. |
| 2009/0216284 A1 | 8/2009 | Chin et al. |
| 2009/0264907 A1 | 10/2009 | Vrba et al. |
| 2009/0306689 A1 | 12/2009 | Welty et al. |
| 2009/0306690 A1 | 12/2009 | Rivers et al. |
| 2009/0318942 A1 | 12/2009 | Shturman |
| 2009/0326568 A1 | 12/2009 | Shturman |
| 2010/0010522 A1 | 1/2010 | Shturman |
| 2010/0030251 A1 | 2/2010 | Sandhu et al. |
| 2010/0063534 A1 | 3/2010 | Kugler et al. |
| 2010/0082051 A1 | 4/2010 | Thorpe et al. |
| 2010/0121361 A1 | 5/2010 | Plowe et al. |
| 2010/0211088 A1 | 8/2010 | Narveson |
| 2010/0228152 A1 | 9/2010 | Fisher |
| 2010/0234864 A1 | 9/2010 | Keller |
| 2010/0241148 A1 | 9/2010 | Schon et al. |
| 2010/0280534 A1 | 11/2010 | Sher |
| 2010/0292720 A1 | 11/2010 | Thatcher et al. |
| 2011/0046543 A1 | 2/2011 | Brandeis |
| 2011/0077673 A1 | 3/2011 | Grubac et al. |
| 2011/0082483 A1 | 4/2011 | Diamant et al. |
| 2011/0087254 A1 | 4/2011 | Welty |
| 2011/0172598 A1 | 7/2011 | Sampognaro et al. |
| 2011/0184447 A1 | 7/2011 | Leibowitz |
| 2011/0213391 A1 | 9/2011 | Rivers et al. |
| 2011/0224625 A1 | 9/2011 | Flickinger et al. |
| 2011/0282354 A1 | 11/2011 | Schulte |
| 2011/0282368 A1 | 11/2011 | Swayze et al. |
| 2011/0301626 A1 | 12/2011 | To |
| 2011/0306995 A1 | 12/2011 | Moberg |
| 2012/0035633 A1 | 2/2012 | Shturman |
| 2012/0035705 A1 | 2/2012 | Giasolli |
| 2012/0046599 A1 | 2/2012 | Schoenle et al. |
| 2012/0046600 A1 | 2/2012 | Kohler et al. |
| 2012/0065639 A1 | 3/2012 | Schmitz |
| 2012/0109170 A1 | 5/2012 | Shturman |
| 2012/0109171 A1* | 5/2012 | Zeroni ............ A61B 17/320758 606/159 |
| 2012/0116431 A1 | 5/2012 | Shturman |
| 2012/0158120 A1 | 6/2012 | Hacker |
| 2012/0165846 A1 | 6/2012 | Shturman |
| 2012/0165847 A1 | 6/2012 | Shturman |
| 2012/0172901 A1 | 7/2012 | Manderfeld |
| 2012/0172903 A1 | 7/2012 | Shturman |
| 2012/0209176 A1 | 8/2012 | Anderson |
| 2012/0232570 A1 | 9/2012 | Jenson et al. |
| 2012/0253372 A1 | 10/2012 | Ross et al. |
| 2012/0259354 A1 | 10/2012 | Kellett |
| 2012/0265229 A1 | 10/2012 | Rottenberg et al. |
| 2013/0005218 A1 | 1/2013 | von Oepen et al. |
| 2013/0010397 A1 | 1/2013 | Ohara et al. |
| 2013/0018398 A1 | 1/2013 | Rivers |
| 2013/0018399 A1 | 1/2013 | Rivers |
| 2013/0023913 A1 | 1/2013 | Rivers |
| 2013/0060234 A1 | 3/2013 | Besser et al. |
| 2013/0072936 A1 | 3/2013 | To et al. |
| 2013/0085514 A1 | 4/2013 | Lee et al. |
| 2013/0092298 A1 | 4/2013 | Bregulla et al. |
| 2013/0103067 A1 | 4/2013 | Fabo et al. |
| 2013/0116655 A1 | 5/2013 | Bacino et al. |
| 2013/0123661 A1 | 5/2013 | Dewaele et al. |
| 2013/0158578 A1 | 6/2013 | Ghodke et al. |
| 2013/0253467 A1 | 9/2013 | Gianotti et al. |
| 2013/0267870 A1 | 10/2013 | Lonky |
| 2013/0296904 A1 | 11/2013 | Shturman |
| 2013/0296905 A1 | 11/2013 | Shturman |
| 2013/0310859 A1 | 11/2013 | Shturman |
| 2013/0317529 A1 | 11/2013 | Golden et al. |
| 2014/0024945 A1 | 1/2014 | Mung et al. |
| 2014/0025044 A1 | 1/2014 | Zamarripa et al. |
| 2014/0039494 A1 | 2/2014 | Kick et al. |
| 2014/0074097 A1 | 3/2014 | Schmitz |
| 2014/0081298 A1 | 3/2014 | Cambronne |
| 2014/0094833 A1 | 4/2014 | Malhi |
| 2014/0100585 A1 | 4/2014 | Anderson et al. |
| 2014/0128893 A1 | 5/2014 | Guggenheimer et al. |
| 2014/0128963 A1 | 5/2014 | Quill |
| 2014/0155990 A1 | 6/2014 | Nyuli |
| 2014/0163664 A1 | 6/2014 | Goldsmith |
| 2014/0180317 A1 | 6/2014 | Shturman |
| 2014/0180319 A1 | 6/2014 | Shturman |
| 2014/0213893 A1 | 7/2014 | Simpson et al. |
| 2014/0214060 A1 | 7/2014 | Bonnette et al. |
| 2014/0222042 A1 | 8/2014 | Kessler et al. |
| 2014/0222045 A1 | 8/2014 | Schneider et al. |
| 2014/0275770 A1 | 9/2014 | Gunday et al. |
| 2014/0276390 A1 | 9/2014 | Eubanks et al. |
| 2014/0276407 A1 | 9/2014 | DeVries et al. |
| 2014/0276684 A1 | 9/2014 | Huennekens et al. |
| 2014/0276696 A1 | 9/2014 | Schneider |
| 2014/0276920 A1 | 9/2014 | Hendrick et al. |
| 2014/0277002 A1 | 9/2014 | Grace |
| 2014/0277011 A1 | 9/2014 | Meader |
| 2014/0296706 A1 | 10/2014 | Chronos et al. |
| 2014/0296742 A1 | 10/2014 | Kalloo et al. |
| 2014/0296868 A1 | 10/2014 | Garrison |
| 2014/0296897 A1 | 10/2014 | Sotak et al. |
| 2014/0303658 A1 | 10/2014 | Bonnette et al. |
| 2014/0316448 A1 | 10/2014 | Higgins |
| 2014/0316449 A1 | 10/2014 | Grothe et al. |
| 2014/0330284 A1 | 11/2014 | Sawada |
| 2014/0330286 A1 | 11/2014 | Wallace |
| 2014/0330366 A1 | 11/2014 | Dehdeshtian |
| 2014/0343538 A1 | 11/2014 | Lenker |
| 2014/0350582 A1 | 11/2014 | Higgins |
| 2014/0358123 A1 | 12/2014 | Ueda et al. |
| 2014/0358156 A1 | 12/2014 | Argentine |
| 2014/0371770 A1 | 12/2014 | Schoenle et al. |
| 2015/0005791 A1 | 1/2015 | Schoenle et al. |
| 2015/0018711 A1 | 1/2015 | Furlong et al. |
| 2015/0032141 A1 | 1/2015 | Silvestro |
| 2015/0032142 A1 | 1/2015 | Silvestro |
| 2015/0038902 A1 | 2/2015 | Mark et al. |
| 2015/0051625 A1 | 2/2015 | Petrucci et al. |
| 2015/0068069 A1 | 3/2015 | Tran et al. |
| 2015/0080795 A1 | 3/2015 | Mattison et al. |
| 2015/0080928 A1 | 3/2015 | Kugler |
| 2015/0088246 A1 | 3/2015 | Astarci et al. |
| 2015/0119909 A1 | 4/2015 | Rydberg |

(56) References Cited

U.S. PATENT DOCUMENTS

| | | |
|---|---|---|
| 2015/0127035 A1 | 5/2015 | Trapp et al. |
| 2015/0133978 A1 | 5/2015 | Paul, Jr. |
| 2015/0142028 A1 | 5/2015 | Ellering et al. |
| 2015/0150587 A1 | 6/2015 | Smith et al. |
| 2015/0150588 A1 | 6/2015 | Rydberg |
| 2015/0157303 A1 | 6/2015 | Brandeis |
| 2015/0164541 A1 | 6/2015 | Shiber |
| 2015/0190622 A1 | 7/2015 | Saab |
| 2015/0201956 A1 | 7/2015 | Higgins et al. |
| 2015/0202044 A1 | 7/2015 | Chau |
| 2015/0209066 A1 | 7/2015 | Dahm et al. |
| 2015/0209072 A1 | 7/2015 | Higgins et al. |
| 2015/0223948 A1 | 8/2015 | Lopez |
| 2015/0224281 A1 | 8/2015 | Kim et al. |
| 2015/0230810 A1 | 8/2015 | Creighton et al. |
| 2015/0230821 A1 | 8/2015 | Batchelor et al. |
| 2015/0238207 A1 | 8/2015 | Cox et al. |
| 2015/0245851 A1 | 9/2015 | McGuckin, Jr. |
| 2015/0258258 A1 | 9/2015 | Bonnette et al. |
| 2015/0265813 A1 | 9/2015 | Xie |
| 2015/0273184 A1 | 10/2015 | Scott et al. |
| 2015/0289902 A1 | 10/2015 | Hehrlein |
| 2015/0290438 A1 | 10/2015 | Gerrans et al. |
| 2015/0313629 A1 | 11/2015 | Shturman |
| 2015/0320971 A1 | 11/2015 | Leeflang et al. |
| 2015/0327884 A1 | 11/2015 | Moberg |
| 2015/0335348 A1 | 11/2015 | Cohen et al. |
| 2015/0342682 A1 | 12/2015 | Bowe |
| 2015/0342718 A1 | 12/2015 | Weber et al. |
| 2015/0351729 A1 | 12/2015 | Chin et al. |
| 2015/0352330 A1 | 12/2015 | Wasdyke et al. |
| 2015/0359595 A1 | 12/2015 | Ben et al. |
| 2015/0374908 A1 | 12/2015 | Piferi |
| 2016/0001062 A1 | 1/2016 | Weber et al. |
| 2016/0015420 A1 | 1/2016 | Higgins et al. |
| 2016/0015434 A1 | 1/2016 | Stieglitz et al. |
| 2016/0022244 A1 | 1/2016 | Courtney et al. |
| 2016/0022296 A1 | 1/2016 | Brady et al. |
| 2016/0022307 A1 | 1/2016 | Wasdyke et al. |
| 2016/0051323 A1 | 2/2016 | Stigall et al. |
| 2016/0058467 A1 | 3/2016 | Shturman |
| 2016/0058468 A1 | 3/2016 | Shturman |
| 2016/0066803 A1 | 3/2016 | Hu et al. |
| 2016/0067465 A1 | 3/2016 | Gerrans et al. |
| 2016/0095733 A1 | 4/2016 | Sharma et al. |
| 2016/0120565 A1 | 5/2016 | Kobayashi et al. |
| 2016/0120570 A1 | 5/2016 | Kobayashi et al. |
| 2016/0128718 A1 | 5/2016 | Aggerholm et al. |
| 2016/0128857 A1 | 5/2016 | Kao |
| 2016/0135796 A1 | 5/2016 | Hundertmark |
| 2016/0136393 A1 | 5/2016 | Tsai et al. |
| 2016/0151639 A1 | 6/2016 | Scharf |
| 2016/0157872 A1 | 6/2016 | Cage et al. |
| 2016/0157886 A1 | 6/2016 | WasDyke et al. |
| 2016/0158490 A1 | 6/2016 | Leeflang et al. |
| 2016/0166265 A1 | 6/2016 | Nita |
| 2016/0174964 A1 | 6/2016 | Tobis |
| 2016/0183963 A1 | 6/2016 | Richter et al. |
| 2016/0183966 A1 | 6/2016 | McGuckin, Jr. |
| 2016/0183968 A1 | 6/2016 | Cambronne |
| 2016/0199091 A1 | 7/2016 | Pigott |
| 2016/0199093 A1 | 7/2016 | Cambronne |
| 2016/0206340 A1 | 7/2016 | Vetter et al. |
| 2016/0213397 A1 | 7/2016 | Shturman |
| 2016/0220399 A1 | 8/2016 | Longo |
| 2016/0228681 A1 | 8/2016 | di Palma et al. |
| 2016/0242790 A1 | 8/2016 | Brandeis |
| 2016/0242805 A1 | 8/2016 | Kohler et al. |
| 2016/0242809 A1 | 8/2016 | Shturman |
| 2016/0249942 A1 | 9/2016 | Olson |
| 2016/0256620 A1 | 9/2016 | Scheckel et al. |
| 2016/0263361 A1 | 9/2016 | Vadivelu et al. |
| 2016/0263391 A1 | 9/2016 | Tasci et al. |
| 2016/0270814 A1 | 9/2016 | Palme et al. |
| 2016/0278805 A1 | 9/2016 | Hatta et al. |
| 2016/0287285 A1 | 10/2016 | Shturman |
| 2016/0287438 A1 | 10/2016 | Badawi et al. |
| 2016/0296683 A1 | 10/2016 | Jin et al. |
| 2016/0302950 A1 | 10/2016 | Marmur |
| 2016/0310709 A1 | 10/2016 | Gotou |
| 2016/0324535 A1 | 11/2016 | Chang et al. |
| 2016/0331394 A1 | 11/2016 | Rottenberg et al. |
| 2016/0338727 A1 | 11/2016 | Bowe |
| 2016/0346003 A1 | 12/2016 | Grothe et al. |
| 2016/0354107 A1 | 12/2016 | Nakano et al. |
| 2016/0354108 A1 | 12/2016 | Nakano et al. |
| 2016/0361528 A1 | 12/2016 | Kanz et al. |
| 2016/0374715 A1 | 12/2016 | McPeak |
| 2016/0375235 A1 | 12/2016 | Schoenle et al. |
| 2017/0000518 A1 | 1/2017 | Smith et al. |
| 2017/0000977 A1 | 1/2017 | Dtorbeck et al. |
| 2017/0027725 A1 | 2/2017 | Argentine |
| 2017/0056169 A1 | 3/2017 | Johnson |
| 2017/0071624 A1 | 3/2017 | McGuckin, Jr. |
| 2017/0079546 A1 | 3/2017 | Costello |
| 2017/0079685 A1 | 3/2017 | Sullivan et al. |
| 2017/0100570 A1 | 4/2017 | Giasolli |
| 2017/0156749 A1 | 6/2017 | Pigott |
| 2017/0164965 A1 | 6/2017 | Chang |
| 2017/0173262 A1 | 6/2017 | Veltz |
| 2017/0273698 A1 | 9/2017 | McGuckin, Jr. et al. |
| 2017/0274270 A1 | 9/2017 | Lundbaek |
| 2017/0348019 A1 | 12/2017 | Nakano et al. |
| 2017/0354435 A1 | 12/2017 | Hatta et al. |
| 2018/0042640 A1 | 2/2018 | Govari et al. |
| 2018/0133436 A1 | 5/2018 | Garrison et al. |
| 2018/0263654 A1 | 9/2018 | Steele et al. |
| 2018/0317952 A1 | 11/2018 | Jamous et al. |
| 2018/0317953 A1 | 11/2018 | Jamous et al. |
| 2018/0317954 A1 | 11/2018 | Jamous et al. |
| 2018/0317955 A1 | 11/2018 | Jamous et al. |
| 2018/0317956 A1 | 11/2018 | Fleming et al. |
| 2019/0038300 A1 | 2/2019 | Savastano et al. |
| 2019/0201052 A1 | 7/2019 | Sahadevan et al. |
| 2019/0247084 A1 | 8/2019 | Spangler et al. |
| 2019/0307483 A1 | 10/2019 | Flury et al. |
| 2019/0357936 A1 | 11/2019 | To et al. |
| 2019/0365412 A1 | 12/2019 | WasDyke et al. |
| 2020/0046403 A1 | 2/2020 | Piippovendsen et al. |
| 2020/0229844 A1 | 7/2020 | Rawson et al. |
| 2020/0261112 A1 | 8/2020 | Jamous et al. |

FOREIGN PATENT DOCUMENTS

| | | |
|---|---|---|
| AU | 2011267862 A1 | 12/2012 |
| AU | 2013316091 A1 | 3/2015 |
| CA | 2648870 | 1/2008 |
| CA | 2722317 | 12/2009 |
| CA | 2800920 A1 | 12/2011 |
| CA | 2883961 A | 3/2014 |
| CN | 102056558 A | 5/2011 |
| CN | 102697534 A | 10/2012 |
| CN | 102946815 A | 2/2013 |
| CN | 102946815 A | 2/2013 |
| CN | 103200886 A | 7/2013 |
| CN | 104955406 A | 9/2015 |
| CN | 205866805 U | 1/2017 |
| DE | 29521096 U1 | 8/1996 |
| EP | 0446932 A2 | 9/1991 |
| EP | 0446932 A3 | 9/1991 |
| EP | 0566426 A1 | 10/1993 |
| EP | 0566656 A1 | 10/1993 |
| EP | 0689468 A1 | 1/1996 |
| EP | 0895458 A2 | 2/1999 |
| EP | 0921761 A1 | 6/1999 |
| EP | 1003425 A1 | 5/2000 |
| EP | 1030705 A2 | 8/2000 |
| EP | 1037560 A1 | 9/2000 |
| EP | 1039864 A1 | 10/2000 |
| EP | 1083829 A1 | 3/2001 |
| EP | 1105049 A2 | 6/2001 |
| EP | 1112103 A2 | 7/2001 |
| EP | 1148900 A1 | 10/2001 |
| EP | 1168965 A1 | 1/2002 |

(56) References Cited

FOREIGN PATENT DOCUMENTS

| | | |
|---|---|---|
| EP | 1187561 A1 | 3/2002 |
| EP | 1250108 A1 | 10/2002 |
| EP | 1274372 A2 | 1/2003 |
| EP | 1343422 A2 | 9/2003 |
| EP | 1377234 A2 | 1/2004 |
| EP | 1776938 B1 | 2/2004 |
| EP | 1302178 B1 | 3/2006 |
| EP | 1660151 A2 | 5/2006 |
| EP | 1673003 A2 | 6/2006 |
| EP | 1708779 A2 | 10/2006 |
| EP | 1737335 A2 | 1/2007 |
| EP | 1755489 A2 | 2/2007 |
| EP | 1761206 A2 | 3/2007 |
| EP | 1874224 A1 | 1/2008 |
| EP | 1879499 A2 | 1/2008 |
| EP | 1887945 A2 | 2/2008 |
| EP | 1897581 A2 | 3/2008 |
| EP | 1906888 A1 | 4/2008 |
| EP | 1983882 A2 | 10/2008 |
| EP | 2024001 A2 | 2/2009 |
| EP | 2040626 A1 | 4/2009 |
| EP | 2040627 A2 | 4/2009 |
| EP | 2040628 A1 | 4/2009 |
| EP | 2010265 A2 | 7/2009 |
| EP | 2079407 A1 | 7/2009 |
| EP | 2099368 A1 | 9/2009 |
| EP | 2155080 A1 | 2/2010 |
| EP | 2155080 B1 | 2/2010 |
| EP | 2203121 A1 | 7/2010 |
| EP | 2280657 A1 | 2/2011 |
| EP | 2282688 A1 | 2/2011 |
| EP | 2303149 A1 | 4/2011 |
| EP | 2303151 A1 | 4/2011 |
| EP | 2398405 A1 | 12/2011 |
| EP | 2579791 A1 | 4/2013 |
| EP | 2280656 B1 | 10/2013 |
| EP | 2742881 A1 | 6/2014 |
| EP | 2819586 A2 | 1/2015 |
| EP | 2895088 A2 | 7/2015 |
| EP | 2298220 B1 | 6/2016 |
| EP | 1887945 B1 | 8/2016 |
| EP | 3141201 A1 | 3/2017 |
| EP | 3166512 A1 | 5/2017 |
| EP | 2967635 B1 | 6/2017 |
| EP | 3366239 A1 | 8/2018 |
| ES | 2482608 T3 | 8/2014 |
| ES | 2594707 T3 | 12/2016 |
| GB | 2426458 A | 11/2006 |
| GB | 2440220 A | 1/2008 |
| GB | 2440221 A | 1/2008 |
| GB | 2440222 A | 1/2008 |
| HK | 1209610 A1 | 4/2016 |
| JP | 2011522597 A | 8/2011 |
| JP | 2013532027 A | 8/2013 |
| JP | 05285768 B2 | 9/2013 |
| JP | 05690928 B2 | 3/2015 |
| JP | 2013532028 | 10/2015 |
| JP | 2015529530 A | 10/2015 |
| KR | 2013018437 A | 2/2013 |
| KR | 1493138 B1 | 2/2015 |
| NL | 1016653 C2 | 5/2002 |
| RU | 2012150415 A | 7/2014 |
| RU | 2538174 C2 | 1/2015 |
| WO | WO1994017739 A1 | 12/1993 |
| WO | WO1994028803 A1 | 12/1994 |
| WO | WO1997043949 A1 | 11/1997 |
| WO | WO1998008554 A1 | 3/1998 |
| WO | WO1999018862 A1 | 4/1999 |
| WO | WO1999018864 A1 | 4/1999 |
| WO | WO1999029240 A1 | 6/1999 |
| WO | WO1999029420 A1 | 6/1999 |
| WO | WO1999035980 A1 | 7/1999 |
| WO | WO1999044516 A1 | 9/1999 |
| WO | WO1999047053 A1 | 9/1999 |
| WO | WO2000056230 A2 | 9/2000 |
| WO | 200195801 A2 | 12/2001 |
| WO | WO2002049518 A2 | 6/2002 |
| WO | WO2002083226 A2 | 10/2002 |
| WO | WO2004073524 A1 | 9/2004 |
| WO | WO2005112834 A2 | 12/2005 |
| WO | WO2006084256 A1 | 8/2006 |
| WO | WO2006126076 A2 | 11/2006 |
| WO | 2008005888 A2 | 1/2008 |
| WO | WO2008006705 A2 | 1/2008 |
| WO | WO2008006706 A1 | 1/2008 |
| WO | WO2008006708 A1 | 1/2008 |
| WO | WO2008062069 A1 | 5/2008 |
| WO | WO2008099424 A2 | 8/2008 |
| WO | WO2008154480 A1 | 12/2008 |
| WO | WO2009146248 A1 | 12/2009 |
| WO | WO2009148805 A1 | 12/2009 |
| WO | WO2009148807 A1 | 12/2009 |
| WO | WO2010002507 A1 | 7/2010 |
| WO | WO2010096140 A1 | 8/2010 |
| WO | WO2010112617 A1 | 10/2010 |
| WO | WO2010112618 A1 | 10/2010 |
| WO | WO2011057060 A2 | 5/2011 |
| WO | WO2011143203 A1 | 11/2011 |
| WO | WO2011159697 A1 | 12/2011 |
| WO | WO2012058438 A1 | 4/2012 |
| WO | 2012058438 A1 | 5/2012 |
| WO | 2013072777 A2 | 5/2013 |
| WO | 2013123007 A1 | 8/2013 |
| WO | WO2013123007 A1 | 8/2013 |
| WO | WO2014022866 A1 | 2/2014 |
| WO | WO2014042752 A2 | 3/2014 |
| WO | WO2014106847 A1 | 7/2014 |
| WO | WO2015006309 A1 | 1/2015 |
| WO | WO2015013590 A1 | 1/2015 |
| WO | WO2015075708 A1 | 5/2015 |
| WO | WO2015148284 A1 | 10/2015 |
| WO | WO2016007652 A1 | 1/2016 |
| WO | WO2016011312 A1 | 1/2016 |
| WO | WO2016019991 A1 | 2/2016 |
| WO | WO2016044406 A1 | 3/2016 |
| WO | WO2016073710 A1 | 5/2016 |
| WO | WO2016108860 A1 | 7/2016 |
| WO | WO2016108880 A1 | 7/2016 |
| WO | WO2016123557 A1 | 8/2016 |
| WO | WO2016126974 A1 | 8/2016 |
| WO | WO2016133931 A1 | 8/2016 |
| WO | WO2016133932 A1 | 8/2016 |
| WO | WO2016150806 A1 | 9/2016 |
| WO | WO2017035381 A1 | 3/2017 |
| WO | WO2014080424 A2 | 5/2017 |
| WO | WO2017109788 A1 | 6/2017 |
| WO | WO2016077758 A1 | 5/2019 |

OTHER PUBLICATIONS

Boston Scientific Convex Burrs, Rotablator, Rotational Atherectomy System Reference Guide, Apr. 2014, 22 pages, Natick, MA.

International Preliminary Report on Patentability for PCT/US2018/030969, Nov. 28, 2019, 9 pages. Geneva, Switzerland.

International Search Report and Written Opinion for PCT Application No. PCT/US2019/050170, Nov. 15, 2019, 15 pages, Europe.

PCT International Preliminary Report on Patentability in Interntional Application No. PCT/US2018/30939, dated Nov. 5, 2019, 8 pages PCT International Preliminary Report on Patentability in Interntional Application No. PCT/US2020/18783, dated Aug. 10, 2021, 7 pages PCT International Search Report and Written Opinion in International Application No. PCT/US2018/030969, dated Jul. 19, 2018, 19 pages.

PCT International Search Report and Written Opinion in International Application No. PCT/US2020/33023, dated Aug. 31, 2020, 14 pages European Office Action from EP Application No. 18729811.2, dated Apr. 21, 2021, 5 pages.

First Chinese Office Action, and translation thereof, from CN Application No. 202110467434.2, dates Sep. 24, 2021, 13 pages.

Non-Final Office Action for U.S. Appl. No. 15/970,736, filed May 6, 2020, 12 pages.

(56) References Cited

OTHER PUBLICATIONS

Chinese Notice of Office Action for Application No. 201880029543.2, Jul. 14, 2022, 16 pages with English translation, China.
European Communication Pursuant to Article 94(3) EPC for Application 18729811.2, Aug. 8, 2022, 5 pages, Munchen, Germany.

* cited by examiner

TISSUE-REMOVING CATHETER WITH GUIDEWIRE ISOLATION LINER

CROSS-REFERENCE TO RELATED APPLICATIONS

The present application is a continuation application of U.S. patent application Ser. No. 15/970,736, which was filed May 3, 2018, which claims the benefit of, and priority to, U.S. Provisional Application Ser. No. 62/500,867, which was filed May 3, 2017, and U.S. Patent Application Ser. No. 62/500,879, which was filed May 3, 2017, each of which is incorporated herein by reference in its entirety for all purposes.

FIELD

The present disclosure generally relates to a tissue-removing catheter, and more particular, to an isolation liner and tissue-removing element for a tissue-removing catheter.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

SUMMARY

In one aspect, a tissue-removing catheter for removing tissue in a body lumen generally comprises an elongate body having an axis, and proximal and distal end portions spaced apart from one another along the axis. The elongate body is sized and shaped to be received in the body lumen. A tissue-removing element is mounted on the distal end portion of the elongate body. The tissue-removing element is configured to remove the tissue as the tissue-removing element is rotated by the elongate body within the body lumen. An inner liner is received within the elongate body and defines a guidewire lumen. The inner liner is coupled to the tissue-removing element at a distal end portion of the inner liner. A coupling assembly is disposed in the tissue-removing element for coupling the inner liner to the tissue-removing element. The coupling assembly comprises a bushing attached directly to the distal end portion of the inner liner.

In another aspect, a tissue-removing catheter for removing tissue in a body lumen generally comprises an elongate body having an axis, and proximal and distal end portions spaced apart from one another along the axis. The elongate body is sized and shaped to be received in the body lumen. A tissue-removing element is mounted on the distal end portion of the elongate body. The tissue-removing element is configured to remove the tissue as the tissue-removing element is rotated by the elongate body within the body lumen. An inner liner is received within the elongate body and defines a guidewire lumen. The inner liner is coupled to the tissue-removing element at a distal end portion of the inner liner. A coupling assembly is disposed in the tissue-removing element for coupling the inner liner to the tissue-removing element. The coupling assembly comprises a bushing attached to the distal end portion of the inner liner. The bushing includes a center ring portion, a proximal ring portion extending proximally from the center ring portion, and a distal ring portion extending distally from the center ring portion. The distal ring portion has a constant outer cross-sectional dimension extending along a length of the distal ring portion.

BRIEF DESCRIPTION OF THE DRAWINGS

Corresponding reference characters indicate corresponding parts throughout the drawings.

DETAILED DESCRIPTION

Figure 1:
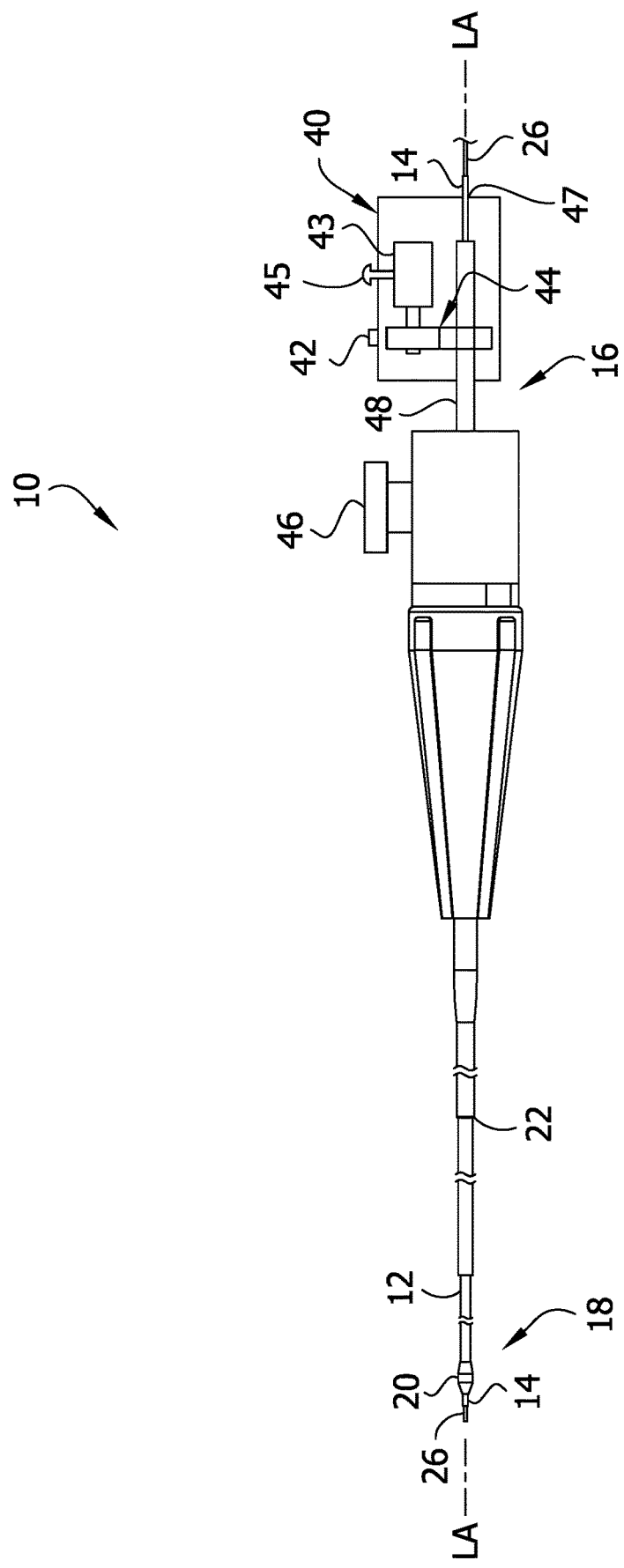
FIG. 1 is an elevation of a catheter of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
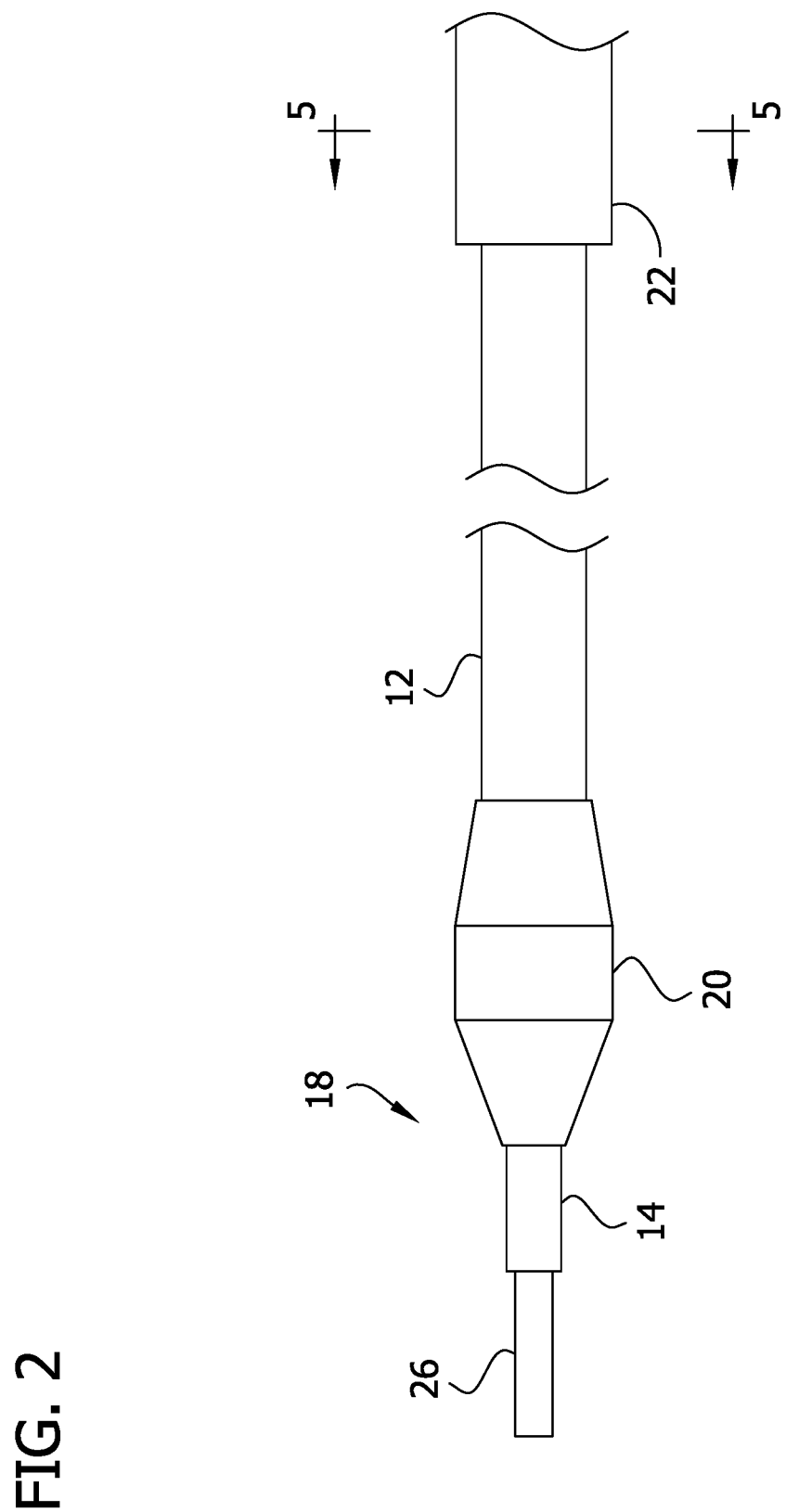
FIG. 2 is an enlarged elevation of a distal end portion of the catheter.
Figure 5:
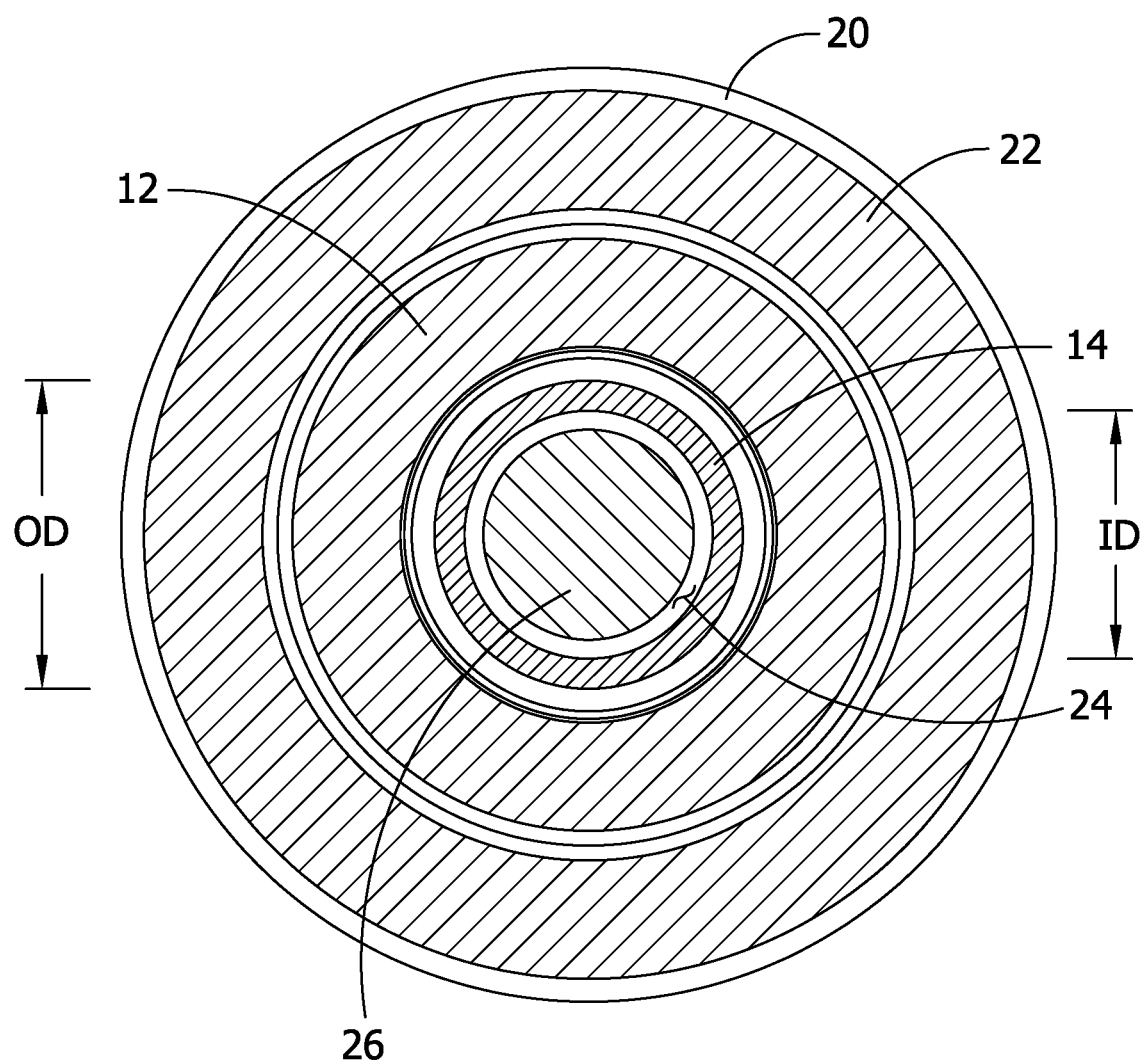
FIG. 5 is a cross section taken through line 5-5 in FIG. 2.
Figure 6:
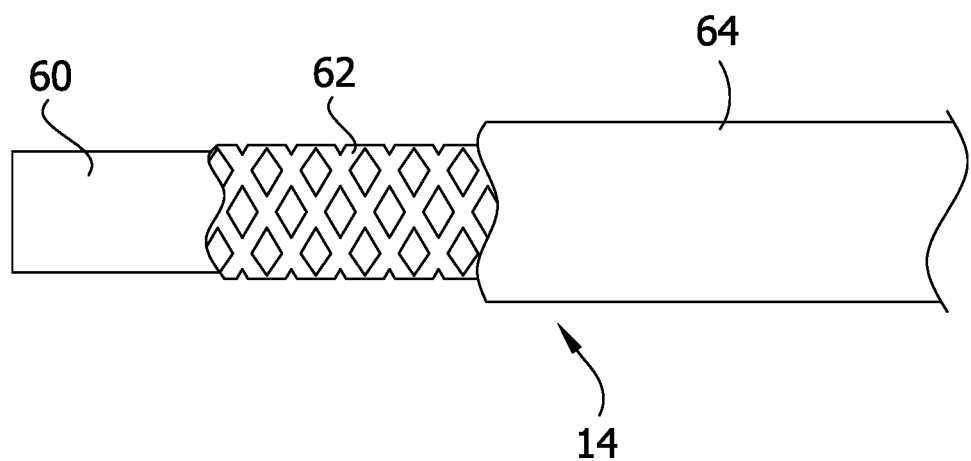
FIG. 6 is a fragmentary elevation of an isolation liner of the catheter with portions broken away to show internal details.

Referring to FIGS. 1 and 2, the catheter 10 comprises an elongate outer layer 12 disposed around an elongate inner liner 14. The outer layer 12 and inner liner 14 extend along a longitudinal axis LA of the catheter from a proximal end portion 16 to a distal end portion 18 of the catheter. A tissue-removing element 20 is disposed on a distal end of the outer layer 12 and is configured for rotation to remove tissue from a body lumen as will be explained in greater detail below. A sheath 22 is disposed around the outer layer 12. The outer layer 12 and the inner liner 14 are both configured to translate relative to the sheath 22. The catheter 10 is sized and shaped for insertion into a body lumen of a subject. The sheath 22 isolates the body lumen from at least a portion of the outer layer 12 and inner liner 14. The inner liner 14 defines a guidewire lumen 24 (FIG. 5) for slidably receiving a guidewire 26 therein so that the catheter 10 can be advanced through the body lumen by traveling along the guidewire. The guidewire can be a standard 0.014 inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends from the proximal end portion 16 through the distal end portion 18 of the catheter 10 such that the guidewire 26 is extendable along an entire working length of the catheter 10. In one embodiment, the overall working length of the catheter 10 may be between about 135 cm (53 inches) and about 142 cm (56 inches).

The catheter 10 further comprises a handle 40 secured at the proximal end portion 16 of the catheter. The handle 40 supports an actuator 42 (e.g., a lever, a button, a dial, a switch, or other device) configured for selectively actuating a motor 43 disposed in the handle to drive rotation of the outer layer 12, and tissue-removing element 20 mounted at the distal end of the outer layer. The motor 43 is coupled to the outer layer 12 by a gear assembly 44 and a drive 48 supported by the handle 40. A slide or advancer 45 is positioned on the handle 40 and operatively coupled to the outer layer 12 for movement of the outer layer relative to the handle to advance and retract the outer layer and tissue-removing element 20. The handle 40 defines a slot (not shown) which limits the movement of the slide 45 relative to the handle. Thus, the length of the slot determines the amount of relative movement between the outer layer 12 and the handle 40. A perfusion port 46 may be disposed at the proximal end 16 of the catheter 10. The port 46 communicates with a space between the sheath 22 and the outer layer 12 for delivering fluid (e.g., saline) to cool the rotating outer layer during use. A proximal port 47 allows for passage of the guidewire 26 and inner liner 14 through the proximal end of the handle 40. A guidewire lock (not shown) may be provided on the handle 40 to lock the guidewire 26 in place relative to the handle.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. In other embodiments, the power supply may come from an external source.

Figure 3:
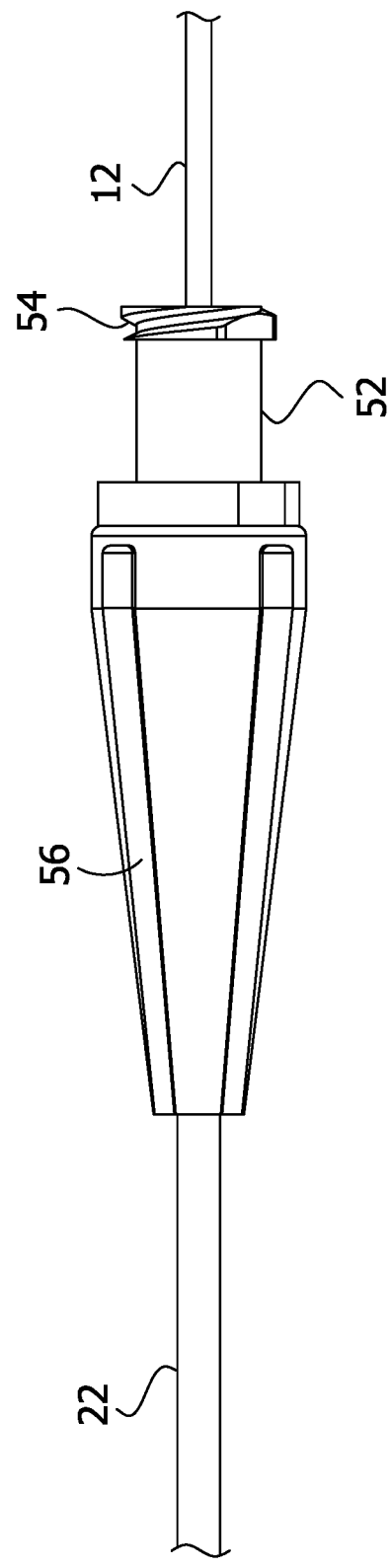
FIG. 3 is an enlarged elevation of a proximal end portion of the catheter.

Referring to FIGS. 1 and 3, the outer sheath 22 comprises a tubular sleeve configured to isolate and protect a subject's arterial tissue within a body lumen from the rotating outer layer 12. The sheath 22 is fixed to the handle 40 at a proximal end of the sheath and does not rotate. A hub 52 mounted on the proximal end of the sheath 22 attaches the sheath to the handle 40. The hub 52 includes a locking feature 54 (e.g., threaded luer lock) for engaging the handle 40 to attach the sheath 22 to the handle. The sheath 22 provides a partial enclosure for the outer layer 12 and inner liner 14 to move within the sheath. The inner diameter of the sheath 22 is sized to provide clearance for the outer layer 12. The space between the sheath 22 and the outer layer 12 allows for the outer layer to rotate within the sheath and provides an area for saline perfusion between the sheath and outer layer. The outer diameter of the sheath 22 is sized to provide clearance with an inner diameter of a guide catheter (not shown) for delivering the catheter 10 to the desired location in the body lumen. A strain relief 56 is provided at the proximal end of the sheath 22 to alleviate tension applied to the proximal end of the sheath 22 as the sheath is bent during use of the catheter 10. In one embodiment, the sheath 22 has an inner diameter of about 0.050 inches (1.27 mm), an outer diameter of about 0.055 inches (1.4 mm), and a length of about 1500 mm (59 inches). The sheath 22 can have other dimensions without departing from the scope of the disclosure. In one embodiment, the outer sheath 22 is made from Polytetrafluoroethylene (PTFE). Alternatively, the outer sheath 22 may comprise a multi-layer construction. For example, the outer sheath 22 may comprise an inner layer of perfluoroalkox (PFA), a middle braided wire layer, and an outer layer of Pebax.

Referring to FIGS. 1, 2, 4, and 5, the outer layer 12 may comprise a tubular stainless steel coil configured to transfer rotation and torque from the motor 43 to the tissue-removing element 20. Configuring the outer layer 12 as a coiled structure provides the outer layer with a flexibility that facilitates delivery of the catheter 10 through the body lumen. Also, the coil configuration allows for the rotation and torque of the outer layer 12 to be applied to the tissue-removing element 20 when the catheter 10 is traversed across a curved path. The stiffness of the outer layer 12 also impacts the ease at which the coil is traversed through the body lumen as well as the coil's ability to effectively transfer torque to the tissue-removing element 20. In one embodiment, the outer layer 12 is relatively stiff such that axial compression and extension of the coil is minimized during movement of the catheter 10 through a body lumen. The coil configuration of the outer layer 12 is also configured to expand its inner diameter when the coil is rotated so that the outer layer remains spaced from the inner liner 14 during operation of the catheter 10. In one embodiment, the outer layer 12 has an inner diameter of about 0.023 inches (0.6 mm) and an outer diameter of about 0.035 inches (0.9 mm). The outer layer 12 may have a single layer construction. For example, the outer layer may comprise a 7 filar (i.e., wire) coil with a lay angle of about 30 degrees. Alternatively, the outer layer 12 could be configured from multiple layers without departing from the scope of the disclosure. For example, the outer layer 12 may comprise a base coil layer and a jacket (e.g., Tecothane™) disposed over the base layer. In one embodiment, the outer layer comprises a 15 filar coil with a lay angle of about 45 degrees. The Tecothane™ jacket may be disposed over the coil. Alternatively, the outer layer 12 may comprise a dual coil layer configuration which also includes an additional jacket layer over the two coil layers. For example, the outer layer may comprise an inner coil layer comprising a 15 filar coil with a lay angle of about 45 degrees, and an outer coil layer comprising a 19 filar coil with a lay angle of about 10 degrees. Outer layers having other configurations are also envisioned.

Referring to FIGS. 1, 2, and 4-6, the inner liner 14 comprises a multiple layer tubular body configured to isolate a least a portion of the guidewire 26 from the outer layer 12 and tissue-removing element 20. The inner liner 14 is extendable through the handle 40 from a position proximal of the handle to a position distal of the handle. In one embodiment, the inner liner 14 is coupled to the handle 40 but is not fixedly attached to the handle 40 to allow translation of the inner liner relative to the handle. In this embodiment, rotation of the inner liner 14 is not prohibited. However, the clearance between the inner liner 14 and the outer layer 12, and the attachment of the inner liner to a coupling assembly 57 in the tissue-removing element 20 prevents any rotation of the inner liner caused by the rotation of the outer layer and tissue-removing element. In this embodiment, both the inner liner 14 and outer layer 12 are permitted to translate relative to the handle 40.

The inner liner 14 has an inner diameter that is sized to pass the guidewire 26. The inner liner 14 protects the guide wire from being damaged by the rotation of the outer layer 12 by isolating the guidewire from the rotatable outer layer. The inner liner 14 also extends past the tissue-removing element 20 to protect the guidewire 26 from the rotating tissue-removing element. Thus, the inner liner 14 is configured to prevent any contact between the guidewire 26 and the rotating components of the catheter 10. Therefore, any metal-to-metal engagement is eliminated by the inner liner 14. This isolation of the outer layer 12 and tissue-removing element 20 from the guidewire 26 also ensures that the rotation of the outer layer and tissue-removing element is not transferred or transmitted to the guidewire. As a result, a standard guidewire 26 can be used with the catheter 10 because the guidewire does not have to be configured to withstand the torsional effects of the rotating components. Additionally, by extending through the tissue-removing element 20 and past the distal end of the tissue-removing element, the inner liner 14 stabilizes the tissue-removing element by providing a centering axis for rotation of the tissue-removing element about the inner liner.

In the illustrated embodiment, the inner liner 14 comprises an inner PTFE layer 60, an intermediate braided layer 62 comprised of stainless steel, and an outer layer 64 of polyimide. The PTFE inner layer 60 provides the inner liner 14 with a lubricous interior which aids in the passing of the guidewire 26 though the inner liner. The braided stainless steel intermediate layer 62 provides rigidity and strength to the inner liner 14 so that the liner can withstand the torsional forces exerted on the inner liner by the outer layer 12. In one embodiment, the intermediate layer 62 is formed from 304 stainless steel. The outer polyimide layer 64 provides wear resistance as well as having a lubricous quality which reduces friction between the inner liner 14 and the outer layer 12. In one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014-inch guidewire 26. The outer diameter OD of the inner liner 14 provides clearance for the outer layer 12 and tissue-removing element 20. Having a space between the inner liner 14 and the outer layer 12 reduces friction between the two components as well as allows for saline perfusion between the components.

Referring to FIGS. 1, 2, 5, and 7, the tissue-removing element 20 extends along the longitudinal axis LA from a proximal end adjacent the distal end portion of the outer layer 12 to an opposite distal end. The tissue-removing element 20 is operatively connected to the motor 43 for being rotated by the motor. When the catheter 10 is inserted into the body lumen and the motor 43 is rotating the tissue-removing element 20, the tissue-removing element is configured to remove occlusive tissue in the body lumen to separate the tissue from the wall of the body lumen. Any suitable tissue-removing element for removing tissue in the body lumen as it is rotated may be used in one or more embodiments. In the illustrated embodiment, the tissue-removing element 20 comprises an abrasive burr configured to abrade tissue in the body lumen when the motor 43 rotates the abrasive burr. The abrasive burr 20 has an abrasive outer surface formed, for example, by a diamond grit coating, surface etching, or the like. In other embodiments, the tissue-removing element can comprise one or more cutting elements having smooth or serrated cutting edges, a macerator, a thrombectomy wire, etc.

Figure 7:
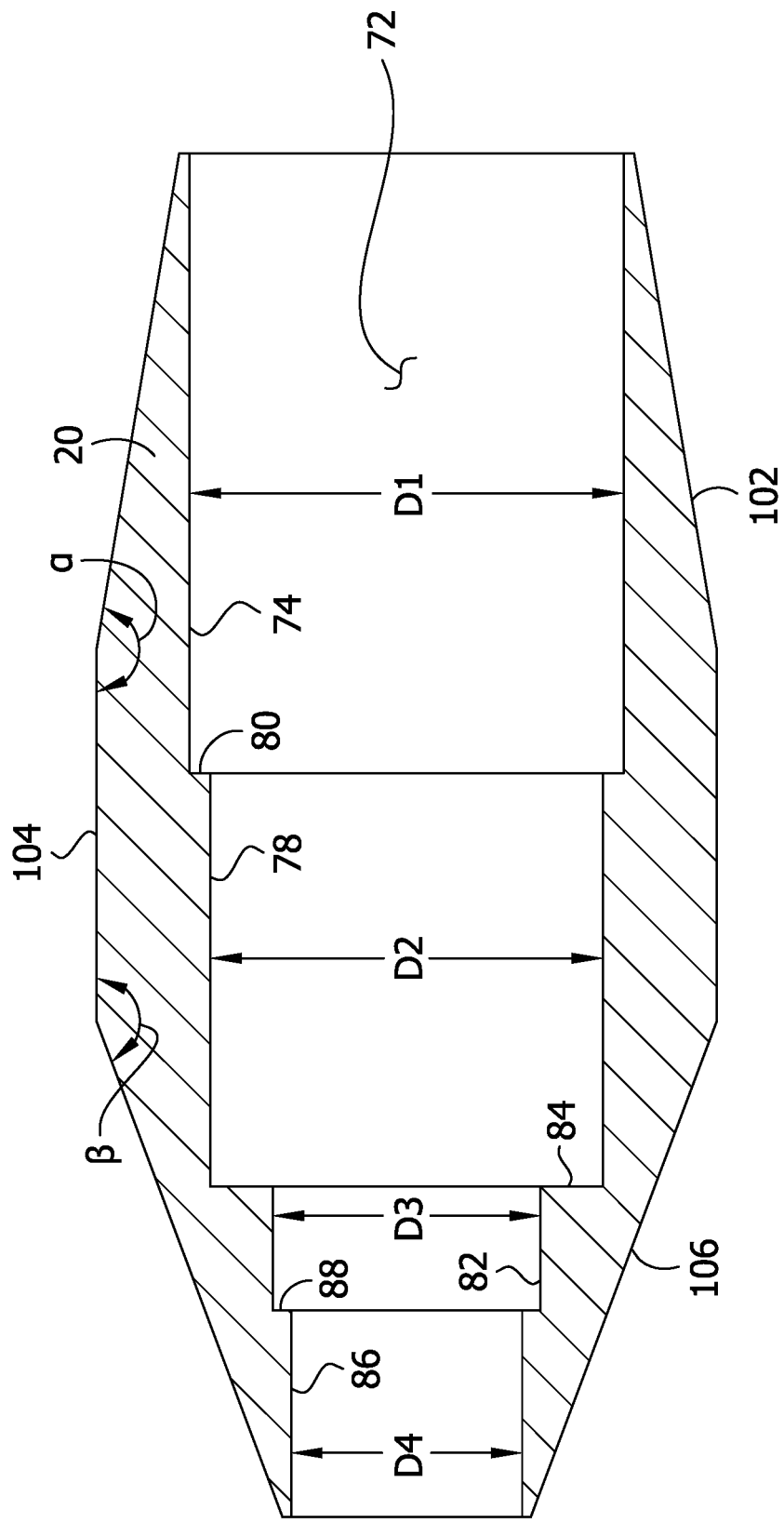
FIG. 7 is an enlarged longitudinal cross section of a tissue-removing element of the catheter.
Figure 8:
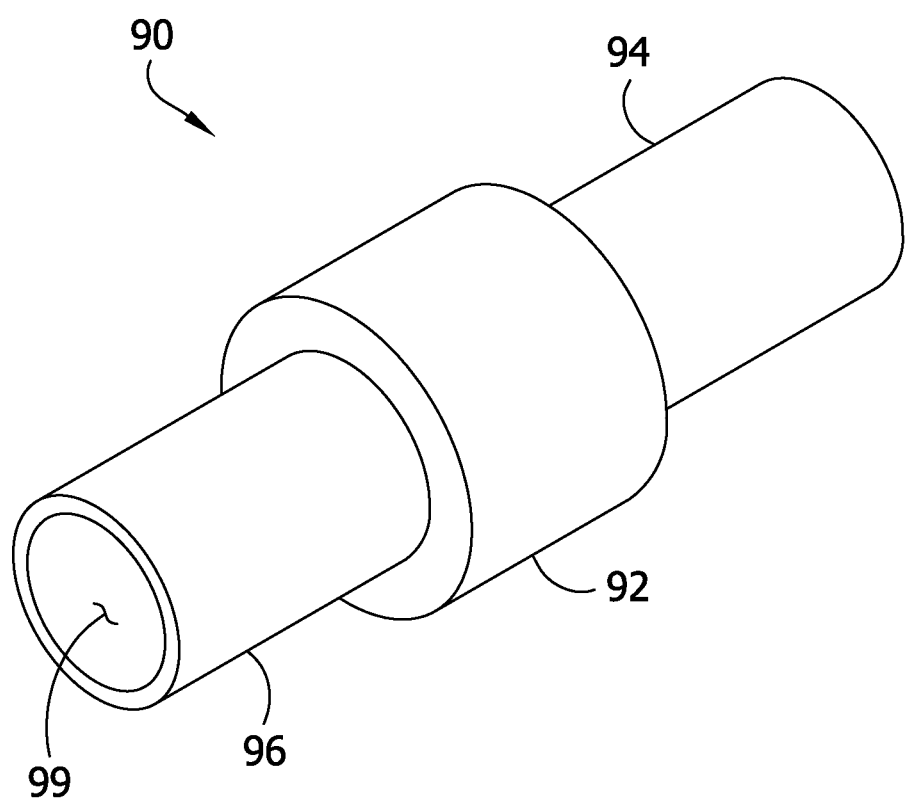
FIG. 8 is a perspective of a bushing of the catheter.
Figure 9:
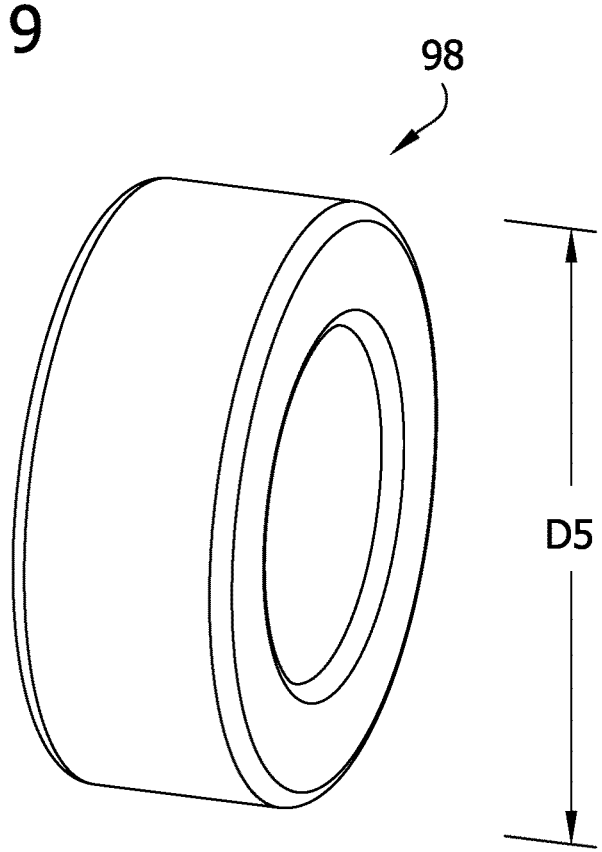
FIG. 9 is a perspective of a first bearing of the catheter.
Figure 10:
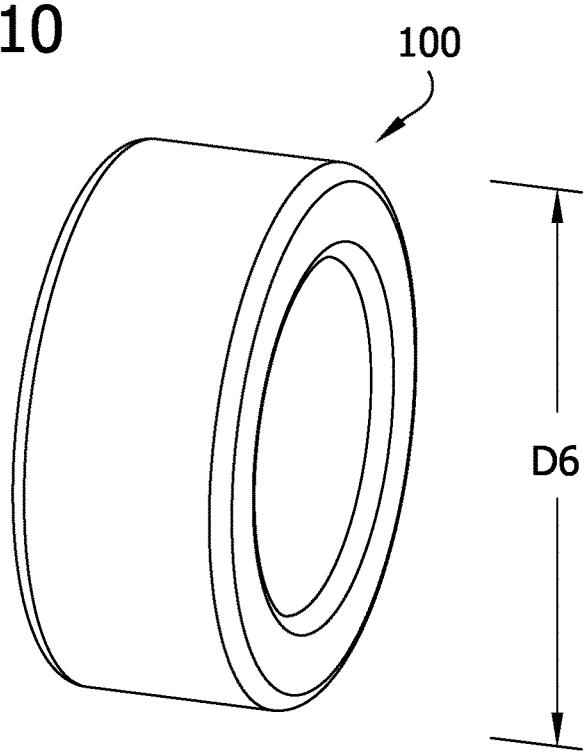
FIG. 10 is a perspective of a second bearing of the catheter.

Referring to FIG. 7, a cavity 72 extends longitudinally through the tissue-removing element 20 such that the tissue-removing element defines openings at its proximal and distal ends. The cavity 72 includes a first diameter portion 74 extending distally from the proximal end of the tissue-removing element 20 and a second diameter portion 78 extending distally from the first diameter portion forming a first shoulder 80 disposed between the first and second diameter portions. A third diameter portion 82 extends distally from the second diameter portion 78 and forms a second shoulder 84 between the second and third diameter portions. A fourth diameter portion 86 extends distally from the third diameter portion to the distal end of the tissue-removing element and forms a third shoulder 88 between the third and fourth diameter portions. The diameters of the first, second, third, and fourth diameter portions 74, 78, 82, 86 are constant along their lengths. In the illustrated embodiment, a diameter D1 of the first diameter portion 74 is larger than a diameter D2 of the second diameter portion 78, the diameter D2 is larger than a diameter D3 of the third diameter portion 82, and the diameter D3 is larger than a diameter D4 of the fourth diameter portion 86. In one embodiment, the diameter D1 of the first diameter portion 74 is about 0.037 inches (0.95 mm), the diameter D2 of the second diameter portion 78 is about 0.035 inches (0.9 mm), the diameter D3 of the third diameter portion 82 is about 0.033 inches (0.85 mm), and the diameter D4 of the fourth diameter portion 86 is about 0.031 inches (0.8 mm). Other cross-sectional dimensions are also envisioned without departing from the scope of the disclosure.

Referring to FIGS. 4 and 7-10, a bushing 90 is received in the cavity 72 of the tissue-removing element 20 and around the inner liner 14. The busing 90 comprises a center ring portion 92, a proximal ring portion 94 extending proximally from the center ring portion, and a distal ring portion 96 extending distally from the center ring portion. The ring portions of the bushing 90 define a channel 99 extending through the bushing that receives a portion of the inner liner 14. In the illustrated embodiment, the center ring portion 92 has a larger outer diameter than the proximal and distal ring portions 94, 96. The center ring portion 92 is disposed in the second diameter portion 78 of the cavity 72, the proximal ring portion 94 is disposed in the first diameter portion 74, and the distal ring portion 96 is disposed in the second and third diameter portions 78, 82. In one embodiment, the bushing 90 is made from polyetheretherketone (PEEK) and polytetrafluoroethylene (PTFE). However, the bushing 90 can be formed from other material without departing from the scope of the disclosure.

A first bearing 98 is disposed around the proximal ring portion 94 of the bearing 90, and a second bearing 100 is disposed around the distal ring portion 96 of the bearing. The first bearing 98 has an outer diameter D5 that is greater than an outer diameter D6 of the second bearing 100. In one embodiment, the bearings 98, 100 are made from Zirconia. The first bearing 98 is disposed in registration with the first diameter portion 74 of the cavity 72 in the tissue-removing element 20 and seats between a distal end of the outer layer 12 at a proximal end of the first bearing, and the center ring portion 92 of the bushing 90 and first shoulder 80 at a distal end of the first bearing. The second bearing 100 is disposed in registration with the second diameter portion 78 of the cavity 72 and is seated between the second shoulder 84 at a distal end of the second bearing, and the center ring portion 92 of the bushing 90 at a proximal end of the second bearing. As such the bushing 90 and bearings 98, 100 are held within the cavity 72 of the tissue-removing element 20. Broadly, the bushing 90 and bearings 98, 100 may be considered a coupling assembly 57 for coupling the inner liner 14 to the tissue-removing element 20.

Figure 4:
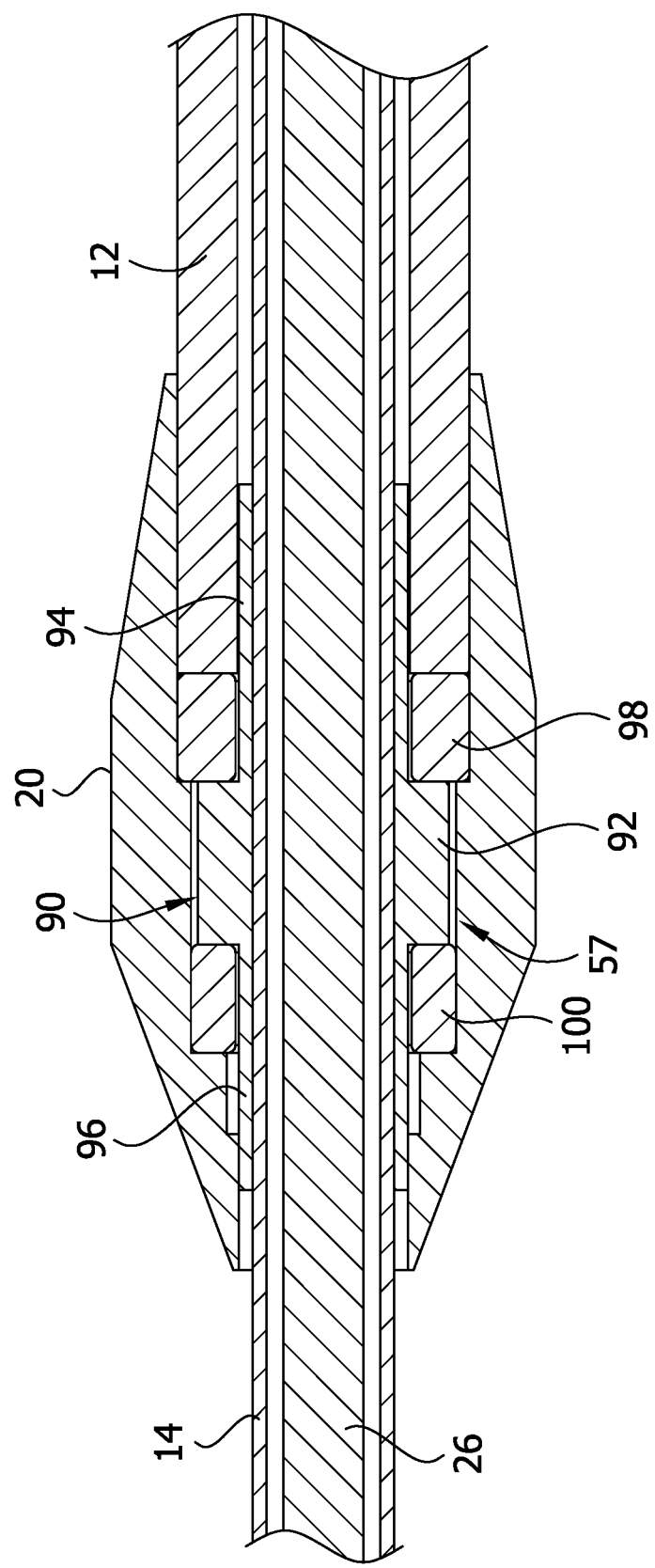
FIG. 4 is an enlarged fragmentary longitudinal cross section of the distal end portion of the catheter in FIG. 2.

Referring to FIG. 4, an interior surface of the bushing 90 is fixedly attached to the inner liner 14 such that the inner liner is coupled to the tissue-removing element 20 through the bushing. In one embodiment an adhesive such as an epoxy glue bonds the bushing 90 to the inner liner 14. As such, the bushing 90 does not rotate around the inner liner 14. The outer layer 12 is directly and fixedly attached to the tissue-removing element 20. The tissue-removing element 20 can be fixedly attached to the distal end of the outer layer 12 by any suitable means. In one embodiment, adhesive bonds the outer layer 12 to the tissue-removing element 20. The outer layer 12 is received in the first diameter portion 74 of the cavity 72 and a distal end of the outer layer abuts the first bearing 98. However, the outer layer 12 is not directly attached to the bushing 90, bearings 98, 100, or inner liner 12. Thus, rotation of the outer layer 12 and tissue-removing element 20 is not transmitted to the inner liner 14 to also rotate the inner liner. Rather the tissue-removing element 20 rotates around the bushing 90 and bearings 98, 100. And because the inner liner is fixedly attached to the bushing 90, which is retained within the cavity 72 of the tissue-removing element 20 by the outer layer 12, the inner liner 14 is coupled to the outer layer through the bushing and bearing arrangement. Therefore, translational movement of the outer layer 12 is transmitted to the inner liner 14 such that the inner liner and outer layer will translate together when one of the inner layer and outer layer is advanced or retracted within the body lumen. This configuration prevents the outer layer 12 and tissue-removing element 20 from advancing past a distal end of the inner liner 14 and contacting the guidewire 26. As a result, a configuration where the inner liner 14 is not positioned to isolate the guidewire 26 from the outer layer 12 and tissue-removing element 20 is prevented.

The inner liner 14 extends through the outer layer 12 and past the distal end of the tissue-removing element 20. The fourth diameter portion 86 of the cavity 72 is sized to pass the inner liner 14 with a small clearance. The inner diameter D4 provides clearance between the tissue-removing element 20 and the inner liner 14 to reduce friction between the components. Accordingly, the tissue-removing element 20 is shaped and arranged to extend around at least a portion of the outer layer 12 and inner liner 14 and thus provides a relatively compact assembly for abrading tissue at the distal end portion of the catheter 10.

Referring to FIG. 7, an exterior surface of the body of the tissue-removing element 20 includes a proximal segment 102, a middle segment 104, and a distal segment 106. A diameter of the proximal segment 102 increases from the proximal end of the tissue-removing element 20 to the middle segment 104. The middle segment has a constant diameter and extends from the proximal segment 102 to the distal segment 106. The diameter of the distal segment 106 tapers from the middle segment 104 to the distal end of the tissue-removing element 20. A transition between the proximal segment 102 and the middle segment 104 forms a first angle $\alpha$ between the proximal and middle segments. In one embodiment, the angle $\alpha$ is less than about 170 degrees. In one embodiment, the angle $\alpha$ is about 165 degrees. Similarly, a transition between the middle segment 104 and the distal segment 106 forms a second angle $\beta$ between the middle and distal segments. In one embodiment, the angle $\beta$ is less than about 170 degrees. In one embodiment, the angle $\beta$ is about 165 degrees. The tapered proximal and distal segments 102, 106 provide the tissue-removing element 20 with a general front and back wedge shaped configuration for wedging apart constricted tissue passages as it simultaneously opens the passage by removing tissue using the abrasive action of the tissue-removing element.

Referring to FIGS. 1 and 2, to remove tissue in the body lumen of a subject, a practitioner inserts the guidewire 26 into the body lumen of the subject, to a location distal of the tissue that is to be removed. Subsequently, the practitioner inserts the proximal end portion of the guidewire 26 through the guidewire lumen 24 of the inner liner 14 and through the handle 40 so that the guidewire extends through the proximal port 47 in the handle. The inner liner 14 may also extend through the handle 40 and out the proximal port 47. With the catheter 10 loaded onto the guidewire 26, the practitioner advances the catheter along the guidewire until the tissue-removing element 20 is positioned proximal and adjacent the tissue. When the tissue-removing element 20 is positioned proximal and adjacent the tissue, the practitioner actuates the motor 43 using the actuator 42 to rotate the outer layer 12 and the tissue-removing element mounted on the outer layer. The tissue-removing element 20 abrades (or otherwise removes) the tissue in the body lumen as it rotates. While the tissue-removing element 20 is rotating, the practitioner may selectively move the outer layer 12 and inner liner 14 distally along the guidewire 26 to abrade the tissue and, for example, increase the size of the passage through the body lumen. The practitioner may also move the outer layer 12 and inner liner 14 proximally along the guidewire 26, and may repetitively move the components in distal and proximal directions to obtain a back-and-forth motion of the tissue-removing element 20 across the tissue. During the abrading process, the bushing 90 and bearings 98, 100 couple the inner liner 14 to the outer layer 12 and allow the outer layer and tissue-removing-element to rotate around the inner liner. The inner liner 14 isolates the guidewire 26 from the rotating outer layer 12 and tissue-removing element 20 to protect the guidewire from being damaged by the rotating components. As such, the inner liner 14 is configured to withstand the torsional and frictional effects of the rotating outer layer 12 and tissue-removing element 20 without transferring those effects to the guidewire 26. Also, the coupling of the inner liner 14 and tissue removing element 20 allows for movement of the inner liner, such as translational movement within the body lumen, to be transmitted to the outer layer 12 and tissue-removing element to move outer layer and tissue-removing element through the body lumen with the inner liner. When the practitioner is finished using the catheter 10, the catheter can be withdrawn from the body lumen and unloaded from the guidewire 26 by sliding the catheter proximally along the guidewire. The guidewire 26 used for the abrading process may remain in the body lumen for use in a subsequent procedure.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
    an elongate body having an axis, and proximal and distal end portions spaced apart from one another along the axis, wherein the elongate body is sized and shaped to be received in the body lumen;
    a tissue-removing element mounted on the distal end portion of the elongate body, the tissue-removing element being configured to remove the tissue as the tissue-removing element is rotated by the elongate body within the body lumen;
    an inner liner received within the elongate body and defining a guidewire lumen, the inner liner being coupled to the tissue-removing element at a distal end portion of the inner liner; and
    a coupling assembly disposed in the tissue-removing element for coupling the inner liner to the tissue-removing element, the coupling assembly comprising a bushing attached directly to the distal end portion of the inner liner, the tissue-removing element extending distally of the coupling assembly.

2. A tissue-removing catheter as set forth in claim 1, wherein the tissue-removing element is rotatable about at least a portion of the bushing.

3. A tissue-removing catheter as set forth in claim 2, wherein the bushing receives a section of the inner liner within a channel of the bushing.

4. A tissue-removing catheter as set forth in claim 3, wherein the bushing comprises a center ring portion, a proximal ring portion extending proximally from the center ring portion, and a distal ring portion extending distally from the center ring portion, the center ring portion having an outer cross-sectional dimension that is larger than an outer cross-sectional dimension of the proximal and distal ring portions.

5. A tissue-removing catheter as set forth in claim 4, wherein the proximal ring portion, center ring portion, and distal ring portion each have constant outer cross-sectional dimensions extending along a length of the bushing.

6. A tissue-removing catheter as set forth in claim 4, wherein the coupling assembly further comprises a bearing disposed around one of the proximal ring portion and the distal ring portion.

7. A tissue-removing catheter as set forth in claim 6, wherein the bushing is made from polyetheretherketone (PEEK) and polytetrafluoroethylene (PTFE) and the bearing is made from Zirconia.

8. A tissue-removing catheter as set forth in claim 1, wherein the bushing comprises a center ring portion, a proximal ring portion extending proximally from the center ring portion, and a distal ring portion extending distally from the center ring portion, the distal ring portion having a constant outer cross-sectional dimension extending along a length of the distal ring portion.

9. A tissue-removing catheter as set forth in claim 8, wherein the distal ring portion has a constant outer cross-sectional dimension extending along an entire length of the distal ring portion.

10. A tissue-removing catheter as set forth in claim 1, wherein a distal end of the inner liner extends distally of the tissue-removing element.

11. A tissue-removing catheter for removing tissue in a body lumen, the tissue-removing catheter comprising:
    an elongate body having an axis, and proximal and distal end portions spaced apart from one another along the axis, wherein the elongate body is sized and shaped to be received in the body lumen;
    a tissue-removing element mounted on the distal end portion of the elongate body, the tissue-removing element being configured to remove the tissue as the tissue-removing element is rotated by the elongate body within the body lumen;
    an inner liner received within the elongate body and defining a guidewire lumen, the inner liner being coupled to the tissue-removing element at a distal end portion of the inner liner; and
    a coupling assembly disposed in the tissue-removing element for coupling the inner liner to the tissue-removing element, the coupling assembly comprising a bushing attached to the distal end portion of the inner liner, the bushing including a center ring portion, a proximal ring portion extending proximally from the center ring portion, and a distal ring portion extending distally from the center ring portion, the distal ring portion having a constant outer cross-sectional dimension extending along a length of the distal ring portion.

12. A tissue-removing catheter as set forth in claim 11, wherein the distal ring portion has a constant outer cross-sectional dimension extending along an entire length of the distal ring portion.

13. A tissue-removing catheter as set forth in claim 11, wherein the proximal ring portion, center ring portion, and distal ring portion each have constant outer cross-sectional dimensions extending along a length of the bushing.

14. A tissue-removing catheter as set forth in claim 11, wherein the center ring portion has an outer cross-sectional dimension that is larger than an outer cross-sectional dimension of the proximal and distal ring portions.

15. A tissue-removing catheter as set forth in claim 11, wherein the tissue-removing element is rotatable about at least a portion of the bushing.

16. A tissue-removing catheter as set forth in claim 11, wherein the bushing includes a channel extending through the bushing, the bushing receiving a section of the inner liner within the channel of the bushing.

17. A tissue-removing catheter as set forth in claim 16, wherein the coupling assembly comprises a bearing disposed around one of the proximal ring portion and the distal ring portion.

18. A tissue-removing catheter as set forth in claim 16, wherein the bushing is made from polyetheretherketone (PEEK) and polytetrafluoroethylene (PTFE) and the bearing is made from Zirconia.

19. A tissue-removing catheter as set forth in claim 11, further comprising a cavity extending through the tissue-removing element from a proximal end to a distal end of the tissue-removing element, wherein the bushing is disposed in the cavity.

20. A tissue-removing catheter as set forth in claim 11, wherein a distal end of the inner liner extends distally of the tissue-removing element.

21. A tissue-removing catheter for removing tissue in a body lumen, the tissue-removing catheter comprising:
- an elongate body having an axis, and proximal and distal end portions spaced apart from one another along the axis, wherein the elongate body is sized and shaped to be received in the body lumen;
- a tissue-removing element mounted on the distal end portion of the elongate body, the tissue-removing element being configured to remove the tissue as the tissue-removing element is rotated by the elongate body within the body lumen;
- an inner liner received within the elongate body and defining a guidewire lumen, the inner liner being coupled to the tissue-removing element at a distal end portion of the inner liner; and
- a coupling assembly disposed in the tissue-removing element for coupling the inner liner to the tissue-removing element, the coupling assembly comprising a bushing attached directly to the distal end portion of the inner liner, wherein a distal end of the inner liner extends distally of the tissue-removing element.

22. A tissue-removing catheter for removing tissue in a body lumen, the tissue-removing catheter comprising:
- an elongate body having an axis, and proximal and distal end portions spaced apart from one another along the axis, wherein the elongate body is sized and shaped to be received in the body lumen;
- a tissue-removing element mounted on the distal end portion of the elongate body, the tissue-removing element being configured to remove the tissue as the tissue-removing element is rotated by the elongate body within the body lumen;
- an inner liner received within the elongate body and defining a guidewire lumen, the inner liner being coupled to the tissue-removing element at a distal end portion of the inner liner; and
- a coupling assembly disposed in the tissue-removing element for coupling the inner liner to the tissue-removing element, the coupling assembly comprising a bushing attached directly to the distal end portion of the inner liner, wherein the bushing comprises a center ring portion, a proximal ring portion extending proximally from the center ring portion, and a distal ring portion extending distally from the center ring portion, and wherein the coupling assembly further comprises a bearing disposed around one of the proximal ring portion and the distal ring portion.

* * * * *